(12) United States Patent
Nakade et al.

(10) Patent No.: US 8,673,889 B2
(45) Date of Patent: Mar. 18, 2014

(54) BLT2-MEDIATED DISEASE, BLT2 BINDING AGENT AND THE COMPOUND

(75) Inventors: Shinji Nakade, Tsukuba (JP);
Tomoyuki Shouno, Mishima-gun (JP);
Takao Shimizu, Bunkyo-ku (JP);
Takehiko Yokomizo, Koshigaya (JP);
Yoshiko Iizuka, Bunkyo-ku (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 661 days.

(21) Appl. No.: 11/587,664

(22) PCT Filed: Apr. 25, 2005

(86) PCT No.: PCT/JP2005/007765
§ 371 (c)(1),
(2), (4) Date: Oct. 26, 2006

(87) PCT Pub. No.: WO2005/102388
PCT Pub. Date: Nov. 3, 2005

(65) Prior Publication Data
US 2008/0132574 A1    Jun. 5, 2008

(30) Foreign Application Priority Data
Apr. 26, 2004  (JP) .............................. P. 2004-129638
Jul. 28, 2004  (JP) .............................. P. 2004-219533

(51) Int. Cl.
*A01N 43/00*    (2006.01)
*A61K 31/33*    (2006.01)
*A61K 9/127*    (2006.01)

(52) U.S. Cl.
USPC ........................................ 514/183; 424/450

(58) Field of Classification Search
USPC ........................................ 514/183; 424/450
See application file for complete search history.

(56) References Cited

U.S. PATENT DOCUMENTS

| | | | | |
|---|---|---|---|---|
| 3,551,414 | A * | 12/1970 | Hawthorne et al. | 540/522 |
| 6,228,985 | B1 | 5/2001 | Blood | |
| 7,300,917 | B2 * | 11/2007 | Nakade et al. | 514/1.7 |
| 7,820,682 | B2 * | 10/2010 | Terakado et al. | 514/264.1 |
| 2004/0034064 | A1 | 2/2004 | Kuduk et al. | |

FOREIGN PATENT DOCUMENTS

| | | |
|---|---|---|
| EP | 0443983 A1 | 8/1991 |
| EP | 1 167 363 A2 | 1/2002 |
| EP | 1270589 A1 | 1/2003 |
| EP | 1 394 147 A1 | 3/2004 |
| EP | 1 553 075 A1 | 7/2005 |
| JP | 2000-505435 A | 5/2000 |
| JP | 2000-505445 A | 5/2000 |
| JP | 2002-030080 A | 1/2002 |
| WO | WO 97/29751 A1 | 8/1997 |
| WO | WO 97/29775 A1 | 8/1997 |
| WO | WO 01/34134 A2 | 5/2001 |
| WO | WO02/34711 * | 5/2002 |
| WO | 02060875 A1 | 8/2002 |
| WO | 02060898 A1 | 8/2002 |
| WO | WO 02/098840 A1 | 12/2002 |
| WO | WO 2004/002530 * | 1/2004 |
| WO | WO 2004/031118 * | 4/2004 |
| WO | WO 2004/031118 A1 | 4/2004 |

OTHER PUBLICATIONS

Soll et. al. (CAS accession # 1994:409300 corresponding to: Bioorganic and Medicinal Chemistry Letters (1993) 3:757-760).*
Saggu et. al. (Journal of the Indian Institute of Science (2002) 82:177-182).*
H. J. Showell et al., "The Preclinical Pharmacological Profile of the Potent and Selective Leukotriene $B_4$ Antagonist CP-195543" (1998) J. Pharmacol. Exp. Ther., vol. 285, No. 3, pp. 946-954.
Takehiko Yokomizo et al., "Hydroxyeicosanoids Bind to and Activate the Low Affinity Leukotriene $B_4$ Receptor, BLT2*" (2001) J. Bio. Chem., vol. 276, No. 15, pp. 12454-12459.
Akiko Toda et al., "Leukotriene B4 receptors" (2002) Prostaglandins & other Lipid Mediators, vol. 68-69, pp. 575-585.
Lars Iversen et al., "Significance of Leukotriene-$A_4$ Hydrolase in the Pathogenesis of Psoriasis" (1997) Skin Pharmacology, vol. 10, No. 4, pp. 169-177.
International Search Report dated Aug. 30, 2005.
Supplementary European Search Report dated Oct. 21, 2009 in European Application No. 05734600.9.
Extended European Search Report dated May 21, 2010, issued in counterpart European Application No. 10150486.8-1223.
Partial European Search Report dated Mar. 5, 2010 in European Application No. 10150486.8.
Iizuka et al., "Characterization of a Mouse Second Leukotriene B4 Receptor, mBLT2," The Journal of Biological Chemistry, vol. 280, No. 26, pp. 24816-24823 (2005).
Neustadt et al., "Construction of a Family of Biphenyl Combinatorial Libraries: Structure-Activity Studies Utilizing Libraries of Mixtures," Bioorganic & Medicinal Chemistry Letters, XP004138238, pp. 2395-2398 (1998).

(Continued)

*Primary Examiner* — Marcos Sznaidman
(74) *Attorney, Agent, or Firm* — Sughrue Mion, PLLC

(57) ABSTRACT

[PROBLEM] The compound that selectively binds to BLT2 and the preventive and/or therapeutic drug for BLT2-mediated disease such as skin disease are needed.
[MEANS FOR SOLVING THE PROBLEMS] The present invention provides the compound with BLT2 binding activity, salt thereof, solvate thereof or prodrug thereof. Since the compound with BLT2 binding activity, particularly the compound represented by the formula (I), (I)

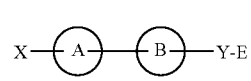

salt thereof, solvate thereof or prodrug thereof (symbols in formula have the same meanings as specification.) have BLT2 binding activity, it is useful for prevention and/or therapy of BLT2 mediated diseases, e.g., dermatosis, intestinal disease, HIV infection, acquired immunodeficiency syndrome, rejection to transplant, transplant rejection, graft-versus-host disease, autoimmune disease, allergic disease, inflammation, infection, ulcers, lymphoma, malignant tumor, leucaemia, arterial sclerosis, hepatitis, hepatic cirrhosis or cancer, etc.

2 Claims, 7 Drawing Sheets

(56) References Cited

OTHER PUBLICATIONS

Peukert et al., "Identification, Synthesis, and Activity of Novel Blockers of the Voltage-Gated Potassium Channel Kv1.5," Journal of Medicinal Chemistry, vol. 46, No. 4, pp. 486-498 (2003).

Eid et al., "Design, Syntheses and Potentiating Activities Against Methicillin Resistant *Staphylococcus aureus* of Cyclic Analogs of LY301621," Bioorganic & Medicinal Chemistry Letters, vol. 7, No. 16, pp. 2087-2092 (1997).

Brandmeier et al., "Antiparallel B-Sheet Conformation in Cyclopeptides Containing a Pseudo-amino Acid with a Biphenyl Moiety," Helvetica Chimica Acta, XP002159083, vol. 77, pp. 70-85 (1994).

Suich et al., "Template-Constrained Cyclic Peptide Analogues of Somatostatin: Subtype-Selective Binding to Somatostatin Receptors and Antiangiogenic Activity," Bioorganic & Medicinal Chemistry, XP002570042, pp. 2229-2241 (2000).

Qian et al., "Design and Synthesis of Non-Peptide Ras CAAX Mimetics as Potent Farnesyltransferase Inhibitors," Journal of Medicinal Chemistry, vol. 39, No. 1, pp. 217-223 (1996).

\* cited by examiner

FIG. 3A
FIG. 3B
FIG. 3C
FIG. 3D
FIG. 3E
FIG. 3F

α KERATIN 5 FL

α KERATIN 5 TL

CONTROL IgG FL

CONTROL gG TL

30 μm

BLT2-MEDIATED DISEASE, BLT2 BINDING AGENT AND THE COMPOUND

TECHNICAL FIELD OF THE INVENTION

The present invention relates to a medical use comprising novel BLT2 mediated disease, a BLT2 binding agent, a novel compound to bind to BLT2 and compound thereof. For details, the present invention relates to a medical use which (1) a preventive and/or therapeutic drug for skin disease comprising the compound to bind to BLT2, salt thereof, solvate thereof and prodrug thereof, (2) the BLT2 binding agent comprising a compound represented by formula (I)

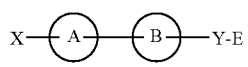

(I)

(in the formula, all symbols have the same meanings as follows), salt thereof, solvate thereof and prodrug thereof as an active ingredients, (3) a compound represented by formula (I-1)

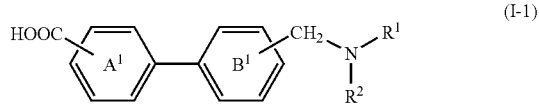

(I-1)

(in the formula, all symbols have the same meanings as follows), salt thereof, solvate thereof and prodrug thereof, and (4) a medical use of the compound represented by formula (I-1), salt thereof, solvate thereof and prodrug thereof.

BACKGROUND OF THE INVENTION

It is thought that Leukotriene B4 (5-[S], 12-[R]-dihydroxy-6,14-cis-8,10-trans-eicosatetraenoic acid; it is abbreviated to LTB4 hereafter.) is a lipid mediator producted by arachidonate cascade and that promotes the migration of leukocytes, the production of active oxygen and the release of lysosomal enzyme, etc., by binding to receptor in the presence of membrane surface, and that plays a key role for organism such as the inflammatory reaction and the defense to bacterial infection etc.

Two kinds of BLT1 and BLT2, which are G-protein coupled receptors, have been already reported as LTB4 receptor (J. Exp. Med., Volume 192, Number 3, 2000, 421-). It has been confirmed that these receptors, which bind to G-protein such as Gi and Gq, etc., cause the induction of intracellular signal such as the rise of intracellular calcium concentration and the suppression of adenylate cyclase activity, etc., by binding of the ligand LTB4. Affinity of LTB4 to both receptors is different though the homology in amino acid sequence between BLT1 and BLT2 is high (45%) and BLT1 specifically strongly binds to LTB4 with Kd value 0.15 nM, BLT2 weakly binds to LTB4 with Kd value 22 nM. It is reported that BLT1 is strongly expressed on leukocyte and is very strictly and organ-specifically expressed, while BLT2 is most strongly expressed in spleen and lymphocyte and sincerely expressed in a lot of organs including liver and ovary.

Thus, because both receptors are different the reactiveness to LTB4 and the expression distribution, it is guessed that both receptors would play a mutually different role in vivo. Therefore, it is thought that a compound that acts on BLT1 shows a pharmacological action different from a compound that acts on BLT2. So far, it has been thought that the compound that acts on BLT1 is useful for diseases including bronchial asthma and articular rheumatism to which leukocytic infiltration relates. On the other hand, it has been thought that the compound that acts on BLT2 is useful for prevention and/or therapy of BLT2 mediated diseases, e.g., human immunodeficiency virus (hereafter, it is abbreviated to HIV) infection, rejection to transplant, transplant rejection, graft-versus-host disease, autoimmune disease (e.g., systemic lupus erythematous, articular rheumatism, myasthenia gravis and sclerosis multiple, etc.), allergic disease (e.g., atopic dermatitis and bronchial asthma, etc.), inflammation, infectious disease, ulcus, lymphoma, carcinoma, leukosis, arteriosclerotic, hepatitis, liver cirrhosis or cancer, etc. However, there is no report that BLT2 is highly expressed in small intestine and skin keratinocyte and that the compound that binds to BLT2 is useful for prevention and/or therapy of intestinal disease including ulcerative colitis or skin disease including psoriasis and dermatitis so far.

And, there is no report about an agonist or antagonist specific to BLT2 and usage thereof at all so for.

On the other hand, it is known that a compound containing biphenyl structure has an antagonism against angiotensin II and a regulatory action on peroxisome proliferator-activated receptor (e.g., see patent literature 1, 2, 3 and 4).

Patent document 1: JP-A-06-72985
Patent document 2: JP-A-06-184086
Patent document 3: JP-A-06-211814
Patent document 4: WO99/12534

DISCLOSURE OF THE INVENTION

Problems to be Solved by the Invention

The present inventors find compounds that bind to BLT2 and are useful as drugs, and newly provide preventive and/or therapeutic drugs for BLT2-mediated diseases including skin disease.

Means for Solving the Problems

The present inventors found that BLT2 is highly expressed in skin keratinocyte and small intestine and that the compound represented by the formula (I), salt thereof, solvate thereof and prodrug thereof has BLT2 binding activity, especially, the compound represented by the formula (I-1), salt thereof, solvate thereof and prodrug thereof has BLT2 binding activity and is useful as a preventive and/or therapeutic drug for BLT2 mediated diseases including skin disease and rejection to transplant to accomplish the present invention as a result of their intensive studies for solving said problems.

That is, the present invention relates to the followings.

(1) An agent for the prevention and/or treatment of skin diseases, which comprises a compound with BLT2 binding activity, a salt thereof, a solvate thereof or a prodrug thereof.

(2) The agent according to (1), wherein the compound with BLT2 binding activity is a compound with agonistic action on BLT2.

(3) The agent according to (1), wherein the compound with BLT2 binding activity is a compound with antagonistic action on BLT2.

(4) The agent according to (1), wherein the skin disease is psoriasis, eczema, skin cancer, keratosis, dyspigmentation or psilosis.

(5) The agent according to (1), wherein the compound with BLT2 binding activity is a compound represented by the formula (I)

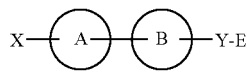

wherein ring A and ring B each independently represent a ring which may be substituted, X represents an acidic group, Y represents a bond or a spacer in which the number of atom in the principal chain is one to three, and E represents an amino group which may be substituted.

(6) The agent according to (5), wherein the compound with BLT2 binding activity is a compound represented by the formula (I-1)

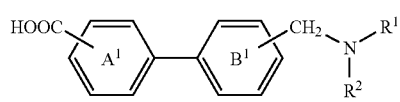

wherein ring $A^1$ and ring $B^1$ each independently represent a benzene ring which may be substituted; and $R^1$ and $R^2$ each independently represent a hydrogen atom or a hydrocarbon group which may be substituted.

(7) A pharmaceutical composition comprising a compound with BLT2 binding activity, a salt thereof, a solvate thereof or a prodrug thereof, in combination with one or more kinds of drugs selected from immunosuppressant, antibiotic, antihistaminic and drenocortical steroid.

(8) A BLT2 binding agent comprising a compound represented by the formula (I)

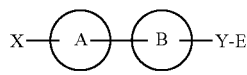

wherein all symbols have the same meanings as described in (5), a salt thereof, a solvate thereof or a prodrug thereof.

(9) The agent according to (8), wherein the BLT2 binding agent is an agonist for BLT2.

(10) The agent according to (8), wherein the BLT2 binding agent is an antagonist for BLT2.

(11) The agent according to (8), which is an agent for the prevention and/or treatment of BLT2-mediated diseases.

(12) The agent according to (11), wherein the BLT2-mediated disease is rejection to transplant, transplant rejection, graft-versus-host disease, autoimmune disease, allergic disease, inflammation, infectious disease, ulcus, lymphoma, carcinoma, leukosis, arteriosclerotic, hepatitis, liver cirrhosis or cancer.

(13) The agent according to (11), wherein the BLT2-mediated disease is intestinal disease or human immunodeficiency virus infection.

(14) A pharmaceutical composition comprising the compound represented by the formula (I) according to (8), a salt thereof, a solvate thereof or a prodrug thereof; in combination with one or more kinds of drugs selected from nonsteroidal antiinflammatory drug, disease-modifying antirheumatic drug, drenocortical steroid, immunosuppressant, antiinflammatory enzyme drug, cartilage protective drug, T lymphocyte inhibitor, TNF-α inhibitor, prostaglandin synthase inhibitor, IL-6 inhibitor, interferon γ agonist, IL-1 inhibitor, EDG-1 agonist, EDG-6 agonist, prostaglandins, phosphodiesterase inhibitor, metalloproteinase inhibitor and chemokine receptor antagonist.

(15) A compound represented by the formula (I-1)

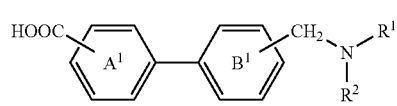

wherein all symbols have the same meanings as described in (6), a salt thereof, a solvate thereof or a prodrug thereof.

(16) A method for the prevention and/or treatment of skin diseases in mammal, which comprises administrating to a mammal an effective amount of a compound with BLT2 binding activity, a salt thereof, a solvate thereof or a prodrug thereof.

(17) Use of a compound with BLT2 binding activity, a salt thereof a solvate thereof or a prodrug thereof for the manufacture of an agent for the prevention and/or treatment of skin diseases.

(18) A method for the prevention and/or treatment of BLT2-mediated diseases in mammal, which comprises administrating to a mammal an effective amount of a compound represented by the formula (I)

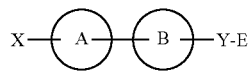

wherein all symbols have the same meanings as described in (5), a salt thereof, a solvate thereof or a prodrug thereof.

(19) Use of a compound represented by the formula (I)

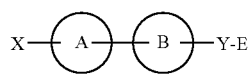

wherein all symbols have the same meanings as described in (5), a salt thereof, a solvate thereof or a prodrug thereof for the manufacture of an agent for the prevention and/or treatment of BLT2-mediated diseases.

In the present specification, the compound with BLT2 binding activity, which specifically binds to BLT2 that is one of LTB4 receptors, only has to be a compound with agonistic or antagonistic action on BLT2, but it is not limited by the structure, the strength of the action or the presence of the specificity.

In the present specification, BLT2 agonist means a compound that shows an action on BLT2 as same as LTB4, but BLT2 antagonist means a compound that antagonizes an action of LTB4 on BLT2. These classifications can be judged by monitoring an event induced by LTB4, e.g., monitoring the rise of the intracellular calcium concentration as described in example using BLT2-expressing cells etc. (e.g., BLT2 over-expressing cells etc.). In particular, for example, if the compound can raise the intracellular calcium concentration in BLT2-expressing cells, it can be judged as BLT2 agonist and if the compound can inhibit the rise of the intracellular calcium concentration by LTB4 in BLT2-expressing cells, it can be judged as BLT2 antagonist.

In the present specification, BLT2 agonist includes a compound in which the rising activity of the intracellular calcium concentration as described in example is less than 100 uM as $EC_{50}$ value. And, BLT2 antagonist includes a compound in which the inhibitory activity of the rise of the intracellular calcium concentration is less than 100 uM as $IC_{50}$ value.

In the present specification, BLT2-mediated disease includes an already found disease and a disease that may be newly found. These diseases include, e.g., skin disease, intestinal disease, HIV transmission, acquired immunodeficiency syndrome, rejection to transplant, transplant abolition, graft-versus-host disease, autoimmune disease, allergic disease, inflammation, infectious disease, ulcus, lymphoma, carcinoma, leukosis, arteriosclerotic, hepatitis, liver cirrhosis and cancer, etc.

In the present specification, skin disease has only to be a disease that meets either requirement in which it is accompanied by the histological laesio in skin tissue or the cytological dysfunction in keratinocyte (especially, skin keratinocyte), it is not limited especially. Concretely, it includes, e.g., eczema, cheloma, lupus skin injury, acne (e.g., comedo etc.), dermatitis (e.g., seborrhoeic dermatitis, solar dermatitis, contact dermatitis, and atopic dermatitis, etc.), psoriasis (e.g., psoriasis vulgaris, guttate psoriasis, pustular psoriasis, psoriasis arthropica, and psoriatic erythrodermia, etc.), keratosis (e.g., seborrhoic keratosis, senile keratosis, actinic keratosis, photic evocation keratosis, and follicular keratosis, etc.), verruca (e.g., condyloma, pointed condyloma, venereal verruga, virus verruga, molluscum contagious, leukoplakia, verruga including human papilloma virus infection (HPV) such as vesicobullous lichen ruber, etc.), and skin cancer (e.g., rodent cancer, cutaneous T lymphoma, and localized benign epidermal tumor (e.g., keratoderma and hard nevus, etc.), etc.), etc. Further, skin disease in the present invention includes a disease accompanied by dysfunction of hair root keratinocyte (e.g., alopecia (e.g., congenital alopecia (diffuse congenital alopecia and alopecia triangularis congenitalis, etc.) and acquired alopecia (folliculitis decalvans, alopecia greata, and follicular mucinosis, etc.), etc.), etc.) and dyspigmentation (e.g., spot, freckle, chromatosis by sunburn, etc.), etc.

In the present specification, intestinal disease includes, e.g., inflammatory bowel disease (e.g., ulcerative colitis and Crohn's disease, etc.), irritable bowel syndrome and colitis, etc.

In the present specification, using the compound with BLT2 binding activity, salt thereof, solvate thereof and prodrug thereof for treatment of skin disease, it is preferable that the compound is bifurcated, depending on whether it is BLT2 agonist or antagonist. Concretely, among said skin diseases, if it is, e.g., alopecia (e.g., congenital alopecia (diffuse congenital alopecia and alopecia triangularis congenitalis, etc.) and acquired alopecia (folliculitis decalvans, alopecia greata, and follicular mucinosis, etc.), etc.) and dyspigmentation (e.g., spot, freckle, chromatosis by sunburn), etc., it is prefer to use BLT2 agonist. If it is, e.g., eczema, cheloma, lupus skin injury, acne (e.g., comedo etc.), dermatitis (e.g., seborrhoeic dermatitis, solar dermatitis, contact dermatitis, and atopic dermatitis, etc.), psoriasis (e.g., psoriasis vulgaris, guttate psoriasis, pustular psoriasis, psoriasis arthropica, and psoriatic erythrodermia, etc.), keratosis (e.g., seborrhoic keratosis, senile keratosis, actinic keratosis, photic evocation keratosis, and follicular keratosis, etc.), verruca (e.g., condyloma, pointed condyloma, venereal verruga, virus verruga, molluscum contagious, leukoplakia, verruga including human papilloma virus infection (HPV) such as vesicobullous lichen ruber, etc.), and skin cancer (e.g., rodent cancer, cutaneous T lymphoma, and localized benign epidermal tumor (e.g., keratoderma and hard nevus, etc.), etc.), etc., it is prefer to use BLT2 antagonist.

In the present invention, the compound with BLT binding activity is preferably the compound represented by formula (I)

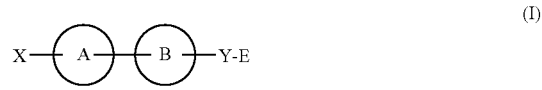

(I)

(wherein, ring A and ring B each independently represent a ring that further may contain substituents, X represents an acidic group, Y represents a bond or a spacer in which the number of atom in the principal chain is one to three, and E represents an amino group that may contain substituents.).

Because the compound represented by formula (I) in the present invention has BLT2 binding activity, they is used for expressing agonistic or antagonistic action accompanied by binding to BLT2.

In the present invention, the ring in the ring that further may contain substituents represented by ring A or ring B includes a bivalent group in which two arbitrary hydrogen atoms are excluded from homocycle or heterocycle.

In the present invention, the homocycle includes, e.g., saturated cyclic hydrocarbon or unsaturated cyclic hydrocarbon, etc. The 3 to 15-membered saturated cyclic hydrocarbon includes, e.g., (a) cycloalkane (e.g., cyclopropane, cyclobutane, cyclopentane, cyclohexane, cycloheptane, cyclooctane, cyclononane, cyclodecane, cycloundecane, cyclododecane, cyclotridecane, cyclotetradecane and cyclopentadecane ring, etc.), (b) saturated polycyclic compound (e.g., perhydropentalene, perhydroazulene, perhydroindene, perhydronaphthalene, perhydroheptalene, spiro[4.4]nonane, spiro[4.5]decane, spiro[5.5]undecane, bicyclo[2.2.1]heptane, bicyclo[3.1.1]heptane, bicyclo[2.2.2]octane, adamantane and noradamantane ring, etc.), etc. Further, the unsaturated cyclic hydrocarbon includes, e.g., 3 to 15-membered unsaturated cyclic hydrocarbon etc. The 3 to 15-membered unsaturated cyclic hydrocarbon includes, e.g., (a) cycloalkene (e.g., cyclopentene, cyclohexane, cycloheptene, cyclooctene, cyclopentadiene, cyclohexadiene, cycloheptadiene and cyclooctadiene ring, etc.), (b) aromatic hydrocarbon (e.g., benzene, azulene, naphthalene, phenanthrene and anthracene ring, etc.), (c) unsaturated polycyclic compound (e.g., pentalene, indene, indane, dihydronaphthalene, tetrahydronaphthalene, heptalene, biphenylene, as-indacene, s-indacene, acenaphthene, acenaphthylene, fluorene, phenalene, bicyclo[2.2.1]hepta-2-en, bicyclo[3.1.1]hepta-2-en and bicyclo[2.2.2]octa-2-en ring, etc.), etc.

In the present specification, the heterocycle includes monocycle or polycyclic heterocycle that may contain 1 to 7 of hetero atom(s) selected from a nitrogen atom, an oxygen atom and a sulfur atom. The monocycle or the polycyclic heterocycle that may contain 1 to 7 of hetero atom(s) selected from a nitrogen atom, an oxygen atom and a sulfur atom includes, e.g., 3 to 15-membered unsaturated monocycle or polycyclic heterocycles and 3 to 15-membered saturated monocycle or polycyclic heterocycles, etc. The 3 to 15-membered unsaturated monocycle or polycyclic heterocycles includes, e.g., (a) aromatic monocyclic heterocycle (e.g., pyrrole, imidazole, triazole, tetrazole, pyrazol, pyridine, pyrazine, pyrimidine, pyridazine, triazine, furan, thiophene, oxazole, isoxazole, thiazole, isothiazole, furazan, oxadiazole and thiadiazole ring, etc.), (b) aromatic fused heterocycle (e.g., indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline and perinidine ring, etc.), (c) Nonaromatic unsaturated heterocycle (e.g., azepine, diazepine, pyran, oxepin, thiopyran, thiepin, oxazine, oxadiazine, oxazepine, oxadiazepine, thiazine, thiadiazine, thiazepine, thiadiazepin, indolizine, dithia naphthalene, quinolizine, chromene, benzoxepin, benzoxazepine, benzoxadiazepine, benzothiepine, benzothiazepine, benzo thiadiazepine, benzazepine, benzodiazepine, xanthene, phenothiazine, phenoxazine, phenoxathiine, thianthrene, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazin, tetrahydropyridazine, tetrahydrotriazine, dihydroazepine, tetrahydroazepine, dihydrodiazepine, tetrahydrodiazepine, dihydrofuran, dihydropyran, dihydrooxepin, tetrahydrooxepin, dihydrothiophene, dihydrothiopyran, dihydro thiepin, tetrahydrothiepin, dihydrooxazole, dihydroisoxazole, dihydrothiazol, dihydroisothiazole, dihydrofurazan, dihydrooxadiazole, dihydrooxazine, dihydro oxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepin, tetrahydrothiadiazepin, indoline, isoindolin, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathian, dihydrobenzooxazine, dihydrobenzothiazine, pyrazinomorpholine, dihydrobenzooxazole, dihydrobenzothiazole, dihydrobenzimidazol, dihydrobenzoazepine, tetrahydrobenzoazepine, dihydrobenzodiazepine, tetrahydrobenzodiazepine, benzodioxepane, dihydrobenzooxazepine, tetrahydrobenzooxazepine, dihydrocarbazole, tetrahydrocarbozole, dihydro-β-carboline, tetrahydro-β-carboline, dihydroacridine, tetrahydroacridine, dihydrodibenzofuran, dihydrodibenzo thiophene, tetrahydrodibenzofuran, tetrahydrodibenzothiophene, dioxanindane, benzodioxan, chroman, benzodithiolane, benzodithiane, 6,7,8,9-tetrahydro-5H-pyrid[4', 3': 4,5]pyrrolo[2,3-b]pyridine, 2,3,4,5-tetrahydro-1H-pyrid[4,3-b]indole, and 6,7,8,9-tetrahydro-5H-pyrid[3', 4': 4,5]pyrrolo[2,3-b]pyridine ring, etc.). And the 3 to 15-membered saturated monocycle or polycyclic heterocycles includes, e.g., aziridine, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, oxirane, oxetane, tetrahydrofuran, tetrahydropyran, perhydrooxepin, thirane, thietane, tetrahydrothiophene, tetrahydrothiopyran, perhydrothiepin, tetrahydrooxazole (oxazolidine), tetrahydroisoxazole (isoxazolidine), tetrahydrothiazole (thiazolidine), tetrahydroisothiazole (isothiazolidine), tetrahydrofurazane, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepin, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydro-β-carboline, perhydroacridine, perhydrodibenzofuran, perhydrodibenzothiophene, dioxolane, dioxane, dithiolane, and dithiane ring, etc.

The ring A or the ring B is preferable to be a bivalent group in which two arbitrary hydrogen atoms are excluded from monocyclic aromatic ring. The monocyclic aromatic ring includes, e.g., benzene ring and said aromatic monocyclic heterocycle, etc., benzene ring is especially preferable.

In the present specificaion, some substituents in the ring that further may contain substituents represented by ring A or ring B include, e.g., [1] a hydrocarbon that may contain substituents (e.g., (a) C1-8 aliphatic hydrocarbon, (b) amino, (c) sulfo, (d) halogen atom, (e) carboxyl, (f) cyano, (g) nitro, (h) oxo, (i) thioxo, (j) hydroxyl, (I) methoxy, (1) trifluoromethyl, and (m) trifluoromethoxy, etc.), [2] a heterocycle that may contain substituents (e.g., (a) C1-8 aliphatic hydrocarbon that may contain substituents (e.g., (1) halogen atom, (2) hydroxyl, (3) trifluoromethyl, (4) trifluoromethoxy, and (5) acetyloxy, etc.), (b) cyclic hydrocarbon that may contain substituents (e.g., (1) halogen atom, (2) hydroxyl, (3) trifluoromethyl, (4) trifluoromethoxy, and (5) acetyloxy, etc.), (c) amino, (d) sulfo, (e) halogen atom, (f) carboxyl, (g) cyano, (h) nitro, (i) oxo, (j) thioxo, (k) hydroxyl, (l) methoxy, (m) methoxycarbonyl, (n) trifluoromethyl, (o) trifluoromethoxy, and (p) acetyl, etc.), [3] an amino that may contain substituents, [4] C1-4 alkylsulfonyl (e.g., methylsulfonyl and ethylsulfonyl, etc.), [5] phenylsulfonyl, [6] halogen atom, [7]carboxyl, [8] cyano, [9] nitro, [10] oxo, [1,1] thioxo, [12] hydroxyl that may be protected, [13] mercapto that may be protected, [14] carbamoyl that may contain substituents, [15] sulfamoyl that may contain substituents, [16] C1-6 alkoxycarbonyl (e.g., methoxycarbonyl, ethoxycarbonyl, and tert-butoxycarbonyl, etc.), [17] sulfo, [18] sulfino, [19] phosphono, [20] amidino, [21] imino, [22] dihydroxyboryl, [23] C1-6 acyl (e.g., formyl, acetyl, propionyl, and butyryl, etc.), etc. The 1 to 5 or 1 to 3 arbitrary substituent(s), which may be same or different when the number of substituents is two or more, may be substituted at the position in which ring A or ring B can be substituted respectively.

In the present specification, the hydrocarbon includes, e.g., [1] aliphatic hydrocarbon, [2]cyclic hydrocarbon, [3]cyclic hydrocarbon-aliphatic hydrocarbon or [4]cyclic hydrocarbon-cyclic hydrocarbon, etc.

In the present specification, the aliphatic hydrocarbon includes, e.g., C1-8 aliphatic hydrocarbon etc. The C1-8 aliphatic hydrocarbon may be linear or branched and includes, e.g., (a) C1-8 alkyl (e.g., methyl, ethyl, propyl, isopropyl, butyl, sec-butyl, tert-butyl, pentyl, hexyl, heptyl, and octyl, etc.), (b) C2-8 alkenyl (e.g., vinyl, propenyl, butenyl, pentenyl, hexenyl, heptenyl, octenyl, butadienyl, pentadienyl, hexadienyl, heptadienyl, octadienyl, hexatrienyl, heptatrienyl, and octatrienyl, etc.), and (c) C2-8 alkynyl (e.g., ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, and octatriynyl, etc.), etc.

In the present specification, the cyclic hydrocarbon means a univalent group in which an arbitrary hydrogen atom is excluded from cyclic hydrocarbon, and includes the same as said homocycle.

In the present specification, the cyclic hydrocarbon-aliphatic hydrocarbon includes one in which said cyclic hydrocarbon binds to said aliphatic hydrocarbon, e.g., (a) C7-16 aralkyl (e.g., benzyl, phenylethyl, phenylpropyl, and naphthalen-1-yl methyl, etc.), (b) C8-16 aralkenyl (e.g., 3-phenyl-2-propenyl, 2-(2-naphthylvinyl) and 4-cyclobutyl-1-butenyl, etc.), (c) (C3-8 cycloalkyl)-(C1-4 alkyl) (e.g., cyclopropylmethyl, cyclohexylmethyl, cyclohexylethyl, cyclohexylpropyl, 1-methyl-1-cyclohexylmethyl, etc.), and (d) (C3-8 cycloalkenyl)-(C1-4 alkyl) (e.g., 3-cyclohexylmethyl etc.), etc.

In the present specification, the cyclic hydrocarbon-cyclic hydrocarbon includes one in which two said cyclic hydrocarbon combine, e.g., 3-phenylphenyl and 4-phenylphenyl, etc.

In the present specification, the C1-8 aliphatic hydrocarbon contained in the substituent of ring A or ring B includes said C1-8 alkyl, said C2-8 alkenyl, and said C2-8 alkynyl, etc.

In the present specification, cyclic hydrocarbon contained in the substituent of ring A or ring B includes a univalent group etc., in which an arbitrary hydrogen atom is excluded from said homocycle.

In the present specification, heterocycle contained in the substituent of ring A or ring B includes a univalent group etc., in which an arbitrary hydrogen atom is excluded from said heterocycle.

In the present specification, the substituent(s) in amino that may contain substituents as the substituent of ring A or ring B include(s), e.g., (a) hydrocarbon that may contain substituents, (b) sulfo, and (c) sulfonyl that binds to hydrocarbon that may contain substituents, etc. Herein, the hydrocarbon that may contain substituents means the same as the hydrocarbon that may contain substituents as the substituent of said ring A or said ring B.

In the present specification, the protecting group in the hydroxyl that may be protected or the mercapto group that may be protected as the substituent of ring A or ring B includes, e.g., a hydrocarbon that may contain substituents. Herein, the hydrocarbon that may contain substituents means the same as the hydrocarbon that may contain substituents as the substituent of said ring A or said ring B.

In the present specification, the substituent(s) in the carbamoyl that may contain substituents or sulfamoyl that may contain substituents as the substituent of ring A or ring B include(s), e.g., a hydrocarbon that may contain substituents etc. Herein, the hydrocarbon group that may contain substituents means the same as the hydrocarbon group that may contain substituents as the substituent of said ring A or said ring B.

In the present specification, the halogen atom includes, e.g., fluorine, chlorine, bromide and iodine, etc.

In the present specification, the sulfo group means —$SO_3H$.

In the present specification, the sulfino group means —$SO_2H$.

In the present specification, the phosphono group means —$PO(OH)_2$.

In the present specification, the dihydroxyboryl group means —$B(OH)_2$.

In the present specification, the acidic group represented by X includes, e.g., [1] hydroxyl, [2] alkoxy, [3] carboxyl, [4] sulfo, [5] sulfino, [6] sulfonamide($SO_2NH_2$ or —$NR^{101}SO_3H$ ($R^{101}$ represents a hydrogen atom or said hydrocarbon.).), [7] phosphono, [8] phenol and [9] various protonic acids that are nitrogen-containing ring residues that contain hydrogen atom(s) that may be deprotonated, etc.

In the present specification, the alkoxy includes, e.g., C1-8 alkoxy etc. The C1-8 alkoxy may be linear or a branched, and includes, e.g., methoxy, ethoxy, propoxy, isopropoxy, butoxy, sec-butoxy, tert-butoxy, pentyloxy, hexyloxy, heptyloxy and octyloxy, etc.

In the present specification, the ring residues containing nitrogen atoms that contain hydrogen atom(s) that may be deprotonated include, e.g.,

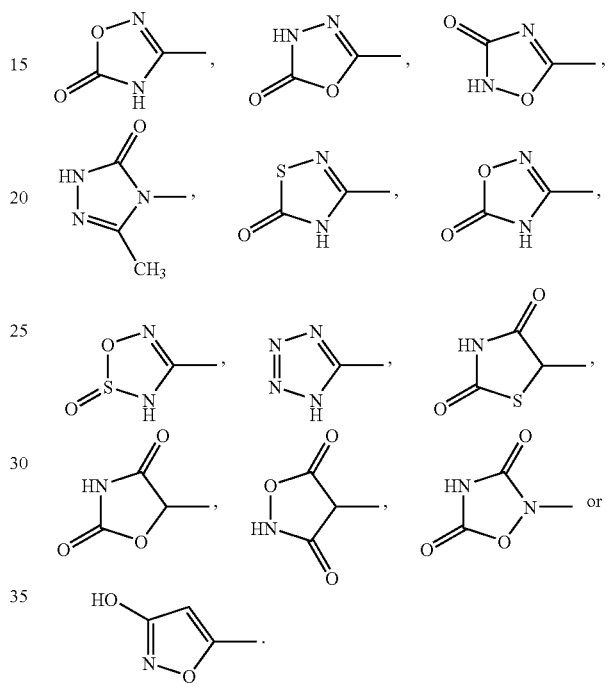

In the present specification, the phenolic group means —$C_6H_4OH$.

The acidic group represented by X is preferable to be carboxyl and

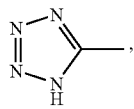

etc. It is more preferable to be carboxyl.

In the present specification, the bond represented by Y means a direct bond without other atoms.

In the present specification, the spacer represented by Y in which the number of atom in the principal chain is one to three means the space in which one to three atom(s) in the principal chain is/are aligned. Herein, the number of atom in the principal chain shall be counted to minimize the number of the atom in the principal chain. For example, the number of 1,2-cyclopentene is two and the number of 1,3-cyclopentene is three. The spacer in which the number of the principal chain is one to three includes, e.g., [1]—O—, [2]—S—, [3]—CO—, [4]—SO—, [5]—$SO_2$—, [6] a nitrogen atom that may contain substituents and [7] a bivalent group in which one to three atom(s) in the principal chain is/are aligned comprising one to three group(s) arbitrarily selected from a group consisting of bivalent C1-3 aliphatic hydrocarbon that may contain substituents. Herein, besides —NH—, the nitrogen atom that may contain substituents represents one in which a hydrogen atom in —NH— is arbitrarily substituted for a hydrocarbon that may contain substituents. Herein, the hydrocarbon in the hydrocarbon that may contain substituents means the same as the above. The substituents in the hydrocarbon that may contain substituents includes, e.g., [a] hydroxyl, [b] oxo, [c] thioxo, [d] halogen atom, [e] cyano, [f] nitro, [g]carboxyl, [h] C1-4 alkoxy(e.g., methoxy, ethoxy, propoxy, isopropoxy, butoxy, sec-butoxy tert-butoxy, etc.), [i] amino and [j] the first or second amino substituted by said aliphatic hydrocarbon etc., and these arbitrary substituents may be substituted at one to eight replaceable position(s), preferably at one to five position(s). The bivalent C1-3 aliphatic hydrocarbon in the bivalent C1-3 aliphatic hydrocarbon that may contain substituents includes, e.g., [a] C1-3 alkylene (e.g., —CH$_2$—, —(CH$_2$)$_2$—, —(CH$_2$)$_3$—, etc.), [b] C2-3 alkenylene (e.g., —CH=CH—, —CH$_2$—CH=CH— and —CH=CH—CH$_2$—, etc.) and [c] C2-3 alkinylene (e.g., —C≡C—, —CH$_2$—C≡C— and —C≡C—CH$_2$—, etc.), etc. The substituents in the bivalent C1-3 aliphatic hydrocarbon that may contain substituents includes, e.g., [a] C1-8 alkyl, [b] C1-8 alkoxy, [c] halogen atom, [d] hydroxyl, [e] oxo, [f] thioxo, [g] amino, [h]=N—OR$_n$(wherein, R$_n$ means the same as the substituents in the nitrogen atom that may contain substituents.), etc., and these arbitrary substituents may be substituted at one to five replaceable. position(s), preferably at one to two position(s).

Y is preferable to be a bivalent C1-3 aliphatic hydrocarbon, more preferable to be methylene.

In the present specification, the substituents in the amino that may contain substituents, which is represented by E, includes, e.g., [1] hydrocarbon that may contain substituents, [2] sulfo and [3] sulfonyl that binds to hydrocarbon that may contain substituents, etc. Herein, the hydrocarbon in the hydrocarbon that may contain substituents means the same as the above. The substituents in the hydrocarbon that may contain substituents includes, e.g., [a] the hydrocarbon that may contain substituents (e.g., (1) C1-4 alkyl(e.g., methyl, ethyl, propyl, isopropyl, butyl, sec-butyl and tert-butyl, etc.), (2) amino, (3) sulfo, (4) halogen atom, (5) carboxyl, (6) cyano, (7) nitro, (8) oxo, (9) thioxo, (10) hydroxyl, (11) methoxy, (12) trifluoromethyl, and (13) trifluoromethoxy, etc.), [b] the heterocycle that may contain substituents (e.g., (1) the hydrocarbon, (2) amino, (3) sulfo, (4) halogen atom, (5) carboxyl, (6) cyano, (7) nitro, (8) oxo, (9) thioxo, (10) hydroxyl, (11) methoxy, (12) trifluoromethyl, (13) trifluoromethoxy, and (14) acetyl, etc.), [c]-NR3R4, [d] C1-4 alkylsulfonyl(e.g., methylsulfonyl and ethylsulfonyl, etc.), [d] C1-4 alkylsulfonyl(e.g., methylsulfonyl and ethylsulfonyl, etc.), [e] phenylsulfonyl, [f] halogen atom, [g]carboxyl, [h] cyano, [i] nitro, [j] oxo, [k] thioxo, and [l]-ORS, [m] mercapto, [n] C1-4 alkylthio(e.g., methylthio, ethylthio, propylthio, isopropylthio, butylthio and tert-butylthio, etc.), [o] phenylthio, [p] carbamoyl, [q] aminocarbonyl substituted by the hydrocarbon (e.g., N-butylaminocarbonyl, N-cyclohexylmethylaminocarbonyl, N-butyl-N-cyclohexylmethylaminocarbonyl, N-cyclohexylaminocarbonyl and phenylaminocarbonyl, etc.), [r] sulfamoyl, [s] aminosulfonyl substituted by the hydrocarbon (e.g., methylamino sulfonyl etc.), [t] aminosulfonyl substituted by the hydrocarbon substituted by amino (e.g., dimethylaminoethylaminosulfonyl and dimethylaminopropyl aminosulfonyl, etc.), [u] C1-6 alkoxycarbonyl(e.g., methoxycarbonyl, ethoxycarbonyl and tert-butoxycarbonyl, etc.), [v] sulfo, [w] sulfino, [x] phosphono, [y] amidino, and [z] imino, [aa] dihydroxyboryl, [bb] C1-4 alkylsulfinyl (e.g., methylsulfinyl and ethylsulfinyl, etc.), [cc] C1-6 acyl(e.g., formyl, acetyl, propionyl and butyryl, etc.), [dd] benzoyl, [ee] hydroxyimino, and [ff] alkyloxyimino(e.g., methyloxyimino and ethyloxyimino, etc.), etc. These arbitrary substituents, which may be same or different respectively when the number of substituents is two or more, may be substituted at one to five replaceable position(s), and each substituent.

In the present specification, R$^3$ and R$^4$ each independently represent [1] hydrogen atom, [2] hydrocarbon that may contain substituent(s), [3] sulfo, [4] sulfonyl that binds to hydrocarbon that may contain substituent(s). Herein, the hydrocarbon in the hydrocarbon that may contain substituent(s) means the same as the above. The substituent(s) in the hydrocarbon that may contain substituent(s) includes, e.g., [a] said hydrocarbon that may contain substituent(s) (e.g., (1) C1-4 alkyl (e.g., methyl, ethyl, propyl, isopropyl, butyl, sec-butyl and tert-butyl, etc.), (2) amino, (3) sulfo, (4) halogen atom, (5) carboxyl, (6) cyano, (7) nitro, (8) oxo, (9) thioxo, (10) hydroxyl, (11) methoxy, (12) trifluoromethyl, and (13) trifluoromethoxy, etc.), [b] said heterocyclic that may contain substituent(s) (e.g., (1) said hydrocarbon, (2) amino, (3) sulfo, (4) halogen atom, (5) carboxyl, (6) cyano, (7) nitro, (8) oxo, (9) thioxo, (10) hydroxyl, (11) methoxy, (12) trifluoromethyl, (13) trifluoromethoxy, (14) acetyl, and (15) methoxycarbonyl, etc.), [c] amino, [d] C$_{1-6}$ acylamino(e.g., acetylamino and propionylamino, etc.), [e] the first or second amino substituted by said hydrocarbon that may be substituted by halogen atom, oxo, amino, and carbamoyl, etc. (e.g., methylamino, ethylamino, propylamino, isopropylamino, butylamino, heptylamino, octylamino, dimethylamino, diethylamino, cyclohexylamino, 1-carbamoylcyclohexyl-2-ethylamino, N-butyl-N-cyclohexylmethylamino, phenylamino, 6,6-dimethylbicyclo[3.1.1]heptylmethylamino, etc.), [f] C1-4 alkylsulfonylamino(e.g., methylsulfonylamino and ethylsulfonylamino, etc.), [g] phenylsulfonylamino, [h] C1-4 alkylsulfonyl(e.g., methylsulfonyl and ethylsulfonyl, etc.), [I]phenylsulfonyl, [j] halogen atom, [k]carboxyl, [l] cyano, [m] nitro, [n] oxo, [o] thioxo, and [p] hydroxyl, [q] C1-10 alkoxy(e.g., methoxy, ethoxy, propoxy, isopropoxy, butoxy, isobutoxy, sec-butoxy, tert-butoxy, decyloxy, cyclohexylmethyloxy, benzyloxy and trifluoromethoxy, etc.) that may be substituted by halogen atom(s), [r] C3-8 cycloalkoxy (e.g., cyclohexyloxy etc.), [s] phenoxy that may be substituted by substituent(s) (e.g., (1) C1-4 alkyl (e.g., methyl, ethyl, propyl, isopropyl, butyl, sec-butyl, and tert-butyl, etc.), (2) halogen atom, (3) trifluoromethyl, and (4) trifluoromethoxy, etc.), [t] 5,6,7,8-tetrahydro-1-naphthyloxy, [u] mercapto, [v] C1-4 alkylthio(e.g., methylthio, ethylthio, propylthio, isopropylthio, butylthio, and tert-butylthio, etc.), [w] phenylthio, [x] carbamoyl, [y] aminocarbonyl substituted by said hydrocarbon (e.g., N-butylaminocarbonyl, N-cyclohexylmethyl aminocarbonyl, N-butyl-N-cyclohexylmethylaminocarbonyl, N-cyclohexylaminocarbonyl, and phenylaminmocarbonyl, etc.), [z] sulfamoyl, [aa] aminosulfonyl substituted by said hydrocarbon (e.g., methylaminosulfonyl etc.), [bb] aminosulfonyl substituted by said hydrocarbon substituted by amino(e.g., dimethylaminoethylaminosulfonyl and dimethylaminopropylaminosulfonyl, etc.), [cc] alkoxycarbonyl(e.g., methoxycarbonyl, ethoxycarbonyl, and tert-butoxycarbonyl, etc.), [dd] sulfo, [ee] sulfino, [ff] phosphono, [gg] amidino, [hh] imino, [ii] dihydroxyboryl, [jj]C1-4 alkylsulfinyl (e.g., methylsulfinyl and ethylsulfinyl, etc.), [kk] C1-6 acyl(e.g., formyl, acetyl, propionyl, and butyryl, etc.), [ll] benzoyl, [mm] hydroxyimino, and [nn] C1-4 alkyloxyimino(e.g., methyloxyimino and ethyloxyimino, etc.), etc. The one to five arbitrary substituent(s), which may be same or different respectively when the number of substituents is two or more, may be substituted at replaceable position(s).

In the present specification, R⁵ represents a hydrogen atom or a hydrocarbon that may contain substituents, which means the same as the hydrocarbon that may contain substituents represented by R³.

Preferable compounds in compounds represented by formula (I) include, e.g., compounds represented by formula (I-1) etc.

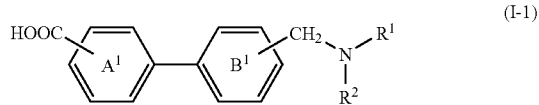

(I-1)

(wherein, ring A¹ and ring B¹ each independently represent a benzene ring that may further contain substituents, and R¹ and R² each independently represent a hydrogen atom or a hydrocarbon that may contain substituents.).

In the present specification, the substituent(s) in the benzene ring that may further contain substituents, which is represented by ring A¹ or B¹, include(s), e.g., said group etc., as substituent(s) of ring A or ring B. The one to five or one to three arbitrary substituent(s), which may be same or different respectively when the number of substituents is two or more, may be substituted at each replaceable position(s) of each benzene ring.

In the present specification, the hydrocarbon in the hydrocarbon that may contain substituents, which is represented by R¹ or R², means the same as the above. The substituent(s) in the hydrocarbon that may contain substituents includes, e.g., [a] said hydrocarbon that may contain substituent(s) (e.g., (1) C1-4 alkyl (e.g., methyl, ethyl, propyl, isopropyl, butyl, sec-butyl and tert-butyl, etc.), (2) amino, (3) sulfo, (4) halogen atom, (5) carboxyl, (6) cyano, (7) nitro, (8) oxo, (9) thioxo, (10) hydroxyl, (11) methoxy, (12) trifluoromethyl, and (13) trifluoromethoxy, etc.), [b] said heterocycle that may contain substituents (e.g., (1) said hydrocarbon, (2) amino, (3) sulfo, (4) halogen atom, (5) carboxyl, (6) cyano, (7) nitro, (8) oxo, (9) thioxo, (10) hydroxyl, (11) methoxy, (12) trifluoromethyl, (13) trifluoromethoxy, and (14) acetyl, etc.), [c]-NR⁶R⁷, [d] halogen atom, [e] oxo, [f] cyano, [g]thioxo and [h]—OR⁸, etc. The one to five arbitrary substituent(s), which may be same or different respectively when the number of substituents is two or more, may be substituted at replaceable position(s) of the hydrocarbon.

In the present specification, R⁶, R⁷ and R⁸ each independently represent a hydrogen atom or a hydrocarbon that may contain substituents. The hydrocarbon in the hydrocarbon that may contain substituents means the same as the above, and the substituent(s) in the hydrocarbon that may contain substituents include(s), e.g., [a] said hydrocarbon that may contain substituent(s) (e.g., (1) C1-4 alkyl (e.g., methyl, ethyl, propyl, isopropyl, butyl, sec-butyl and tert-butyl, etc.), (2) amino, (3) sulfo, (4) halogen atom, (5) carboxyl, (6) cyano, (7) nitro, (8) oxo, (9) thioxo, (10) hydroxyl, (11) methoxy, (12) trifluoromethyl, and (13) trifluoromethoxy, etc.), [b] said heterocycle that may contain substituents (e.g., (1) said hydrocarbon, (2) amino, (3) sulfo, (4) halogen atom, (5) carboxyl, (6) cyano, (7) nitro, (8) oxo, (9) thioxo, (10) hydroxyl, (11) methoxy, (12) trifluoromethyl, (13) trifluoromethoxy, and (14) acetyl,(15) methoxycarbonyl, etc.), [c] halogen atom, [d]carboxyl, [e] cyano, [f] nitro, [g] oxo, [h] hydroxyl, [i] C1-10 alkoxy that may be substituted by halogen atoms (e.g., methoxy, ethoxy, propoxy, isopropoxy, butoxy, isobutoxy, sec-butoxy, tert-butoxy, decyloxy, cyclohexylmethyloxy, benzyloxy and trifluoromethoxy, etc.), [j]C1-4 alkylthio (e.g., methylthio, ethylthio, propylthio, isopropylthio, butylthio and tert-butylthio, etc.), and [k] C1-6 alkoxycarbonyl(e.g., methoxycarbonyl, ethoxycarbonyl and tert-butoxycarbonyl, etc), etc.

Preferable compounds in compounds represented by formula (I-1) include, e.g., the compound described in examples.

Further, preferable compounds in compounds represented by formula (I) include, e.g., compounds represented by the following (1) to (46), salts thereof, solvates thereof, and prodrugs thereof, etc.

(1)  O-(tert-butyl)-N-[(pentyl{[2'-(1H-tetrazol-5-yl)biphenyl-4-yl]methyl}amino)carbonyl]serine,
(2)  N-[(pentyl{[2'-(1H-tetrazol-5-yl)biphenyl-4-yl]methyl}amino)carbonyl]serine,
(3)  N-butyl-N'-[2-(4-methoxyphenyl)ethyl]-N-{[2'-(1H-tetrazol-5-yl)biphenyl-4-yl]methyl}urea,
(4)  diethyl{[(butyl{[2'-(1H-tetrazol-5-yl)biphenyl-4-yl]methyl}amino)carbonyl]amino}(2-cyanoethyl)malonate,
(5)  N-butyl-N'-(2-phenylethyl)-N-{[2'-(1H-tetrazol-5-yl)biphenyl-4-yl]methyl}urea,
(6)  N-butyl-N'-(2,2-diphenylethyl)-N-{[2'-(1H-tetrazol-5-yl)biphenyl-4-yl]methyl}urea,
(7) N-butyl-N'-isopropyl-N-{[2'-(1H-tetrazol-5-yl)biphenyl-4-yl]methyl}urea,
(8) methyl 2-{[(butyl {[2'-(1H-tetrazol-5-yl)biphenyl-4-yl]methyl}amino)carbonyl]oxy}-3-phenylpropanoate,
(9) N-butyl-N'-[2-(4-hydroxyphenyl)ethyl]-N-{[2'-(1H-tetrazol-5-yl)biphenyl-4-yl]methyl}urea,
(10) methyl N-[(butyl {[2'-(1H-tetrazol-5-yl)biphenyl-4-yl]methyl}amino)carbonothioyl]glycinate,
(11)  N,N'-dibutyl-N-{[2'-(1H-tetrazol-5-yl)biphenyl-4-yl]methyl}urea,
(12) N-butyl-N'-cyclohexyl-N-{[2'-(1H-tetrazol-5-yl)biphenyl-4-yl]methyl}urea,
(13)  N-butyl-N'-phenyl-N-{[2'-(1H-tetrazol-5-yl)biphenyl-4-yl]methyl}urea,
(14)  decyl N-[(butyl{[2'-(1H-tetrazol-5-yl)biphenyl-4-yl]methyl}amino)carbonyl]tyrosinate,
(15)  N'-biphenyl-2-yl-N-butyl-N-{[2'-(1H-tetrazol-5-yl)biphenyl-4-yl]methyl}urea,
(16)  N-butyl-N'-(3-methoxyphenyl)-N-{[2'-(1H-tetrazol-5-yl)biphenyl-4-yl]methyl}urea,
(17)  N-butyl-N'-(4-methoxyphenyl)-N-{[2'-(1H-tetrazol-5-yl)biphenyl-4-yl]methyl}urea,
(18)  ethyl 2-{[(butyl{[2'-(1H-tetrazol-5-yl)biphenyl-4-yl]methyl}amino)carbonyl]amino}benzoate,
(19)  ethyl 3-{[(butyl{([2'-(1H-tetrazol-5-yl)biphenyl-4-yl]methyl}amino)carbonyl]amino}benzoate,
(20) N-butyl-N'-(4-methylphenyl)-N-{[2'-(1H-tetrazol-5-yl)biphenyl-4-yl]methyl}urea,
(21) N-butyl-N'-[(1S)-1-phenylethyl]-N-{[2'-(1H-tetrazol-5-yl)biphenyl-4-yl]methyl}urea,
(22)  N'-benzyl-N-butyl-N-{[2'-(1H-tetrazol-5-yl)biphenyl-4-yl]methyl}urea,
(23)  N-butyl-N'-(3-ethylphenyl)-N-{[2'-(1H-tetrazol-5-yl)biphenyl-4-yl]methyl}urea,
(24) ethyl N-benzyl-N-[(butyl{[2'-(1H-tetrazol-5-yl)biphenyl-4-yl]methyl}amino)carbonyl]glycinate,
(25)  N-butyl-N'-(4-ethylphenyl)-N-{[2'-(1H-tetrazol-5-yl)biphenyl-4-yl]methyl}urea,
(26) N'-(2-bromophenyl)-N-butyl-N-{[2'-(1H-tetrazol-5-yl)biphenyl-4-yl]methyl}urea,
(27)  N'-biphenyl-4-yl-N-butyl-N-{[2'-(1H-tetrazol-5-yl)biphenyl-4-yl]methyl}urea,

(28) N-butyl-N'-(2-ethoxyphenyl)-N-{[2'-(1H-tetrazol-5-yl)biphenyl-4-yl]methyl}urea,
(29) N-butyl-N-{[2'-(1H-tetrazol-5-yl)biphenyl-4-yl]methyl}-N'-[4-(trifluoromethoxy)phenyl]urea,
(30) N-butyl-N'-(3,4-difluorophenyl)-N-{[2'-(1H-tetrazol-5-yl)biphenyl-4-yl]methyl}urea,
(31) N-butyl-N'-(2,6-diisopropylphenyl)-N-{[2'-(H-tetrazol-5-yl)biphenyl-4-yl]methyl}urea,
(32) ethyl N-[(butyl{[2'-(1H-tetrazol-5-yl)biphenyl-4-yl]methyl}amino)carbonyl]-O-ethyl-α-methyltyrosinate,
(33) N-butyl-N'-(2-nitrophenyl)-N-{[2'-(1H-tetrazol-5-yl)biphenyl-4-yl]methyl}urea,
(34) ethyl[(butyl{[2'-(1H-tetrazol-5-yl)biphenyl-4-yl]methyl}amino)carbonyl]carbamate,
(35) methyl 3-{[(butyl{[2'-(1H-tetrazol-5-yl)biphenyl-4-yl]methyl}amino)carbonyl]amino}thiophen-2-carboxylate,
(36) N-butyl-N'-[(1R)-1-phenylethyl]-N-{[2'-(H-tetrazol-5-yl)biphenyl-4-yl]methyl}urea,
(37) N-butyl-N'-(4-methyl-2-nitrophenyl)-N-{[2'-(1H-tetrazol-5-yl)biphenyl-4-yl]methyl}urea,
(38) N-butyl-N'-[1-(3-isopropenylphenyl)-1-methylethyl]-N-{[2'-(1H-tetrazol-5-yl)biphenyl-4-yl]methyl}urea,
(39) N-butyl-N'-(2-hydroxyphenyl)-N-{[2'-(1H-tetrazol-5-yl)biphenyl-4-yl]methyl}urea,
(40) 2-{[(butyl{[2'-(1H-tetrazol-5-yl)biphenyl-4-yl]methyl}amino)carbonyl]amino}-4,5,6,7-tetrahydro-1-benzothiophen-3-carboxylic acid,
(41) ethyl 2-{[(butyl{[2'-(1H-tetrazol-5-yl)biphenyl-4-yl]methyl}amino)carbonyl]amino}-4-nitrobenzoate,
(42) methyl N-[(butyl{[2'-(1H-tetrazol-5-yl)biphenyl-4-yl]methyl}amino)carbonyl]-N-(cyclohexylmethyl)glycinate,
(43) N-butyl-N'-(tetrahydrofuran-2-ylmethyl)-N-{[2'-(1H-tetrazol-5-yl)biphenyl-4-yl]methyl}urea,
(44) N-butyl-N-{[2'-(1H-tetrazol-5-yl)biphenyl-4-yl]methyl}-3,4-dihydroquinolin-1(2H)-carboamide,
(45) N-butyl-N'-(2-morpholin-4-ylethyl)-N-{[2'-(1H-tetrazol-5-yl)biphenyl-4-yl]methyl}urea, or
(46) N-butyl-N'-[2-(methylthio)phenyl]-N-{[2'-(1H-tetrazol-5-yl)biphenyl-4-yl]methyl}urea.

In the above compounds, the compound (5), (7), (9), (10), (11), (12), (13), (16), (17), (19), (20), (21), (22), (30), (34), (39), (40), (43), and (45) have BLT2 agonistic activity and other compounds have BLT2 antagonistic activity.

Isomers

Unless otherwise specifically mentioned, the present invention includes all isomers. For example, alkyl, alkenyl, alkynyl, alkyloxy, alkoxy, alkenyloxy, alkynyloxy, alkylthio, alkylsulfinyl, alkylsulfonyl, alkylene, alkenylene, alkynylene, acyl and acyloxy include linear and branched ones. Further, the present invention includes all isomers due to double bond, ring and fused ring (E-, Z-, cis- and trans-substances), isomers due to presence of asymmetric carbon etc. (R-, S-, α- and β-substances, enantiomer, and diastereomer), optically active substances having optical rotation (D-, L-, d-, and l-substances), polar substances by chromatographic separation (high-polar substance and low-polar substance), equilibrium compounds, rotational isomers, a mixture thereof in any proportion and a racemic mixture. Further, the present invention also includes all isomers including tautomers.

Salts and Solvates

Salts of the compound represented by formula (I) include all salts allowed in pharmacology. The salts allowed in pharmacology are preferable to be little toxic and water-soluble. The suitable salts include, e.g., alkali metal salts (e.g., potassium, sodium and lithium, etc.), alkaline earth metal salts (e.g., calcium and magnesium, etc.), ammonium salts (e.g., tetramethylammonium and tetrabutylammonium, etc.), organic amine salts (e.g., triethylamine, methylamine, dimethylamine, cyclopentylamine, benzylamine, phenethylamine, piperidine, monoethanolamine, diethanolamine, tris (hydroxymethyl)methylamine, lysine, arginine and N-methyl-D-glucamine, etc.), acid-addition salts (e.g., inorganic acid salts (e.g., hydrochloride, hydrobromate, hydroiodate, sulfate, phosphate and nitrate, etc.), organic acid salts (e.g., acetate, trifluoroacetate, lactate, tartrate, oxalate, fumarate, maleate, benzoate, citrate, methane sulfonate, ethane sulfonate, benzene sulfonate, toluene sulfonate, isethionate, glucuronate and gluconate, etc.), etc.

Further, the salts include quaternary ammonium salt. The quaternary ammonium salt represents one in which nitrogen atoms of the compound represented by formula (I) were quaternarized by $R^O$. $R^O$ represents C1-8 alkyl substituted with C1-8 alkyl or phenyl. The solvates of the compound represented by formula (I) include, e.g., solvates such as water and alcohols solvents (e.g., methanol and ethanol, etc.). The solvates are preferable to be little toxic and water-soluble. Further, the solvates of the compounds of the present invention include solvates of alkaline (earth) metal salts, ammonium salt, organic amine salts or acid-addition salts of the above compounds of the present invention. The present invention compounds may be converted into the above salts and solvates by known methods.

Prodrugs

The prodrug of the compound represented by formula (I) means a compound that is converted into the compound represented by formula (I) by enzymes or gastric acid, etc., in vivo. The prodrug of the compound represented by formula (I) includes compounds in which the amino was, e.g., acylated, alkylated or phosphorylated (e.g., the compounds in which the amino of the compound represented by formula (I) was eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated and acetoxymethylated tert-butylated, etc.) when the compound represented by formula (I) has amino(s); the compounds in which the hydroxyl was, e.g., acylated, alkylated, phosphorylated or borated (e.g., the compounds in which the hydroxyl of the compound represented by formula (I) was acetylated, palmitoylated, propanoylated, pivaloylated, succinylated, fumarylated, alanylated or dimethylaminomethylcarbonylated) when the compound represented by formula (I) has a hydroxyl; the carboxyl of the compound represented by formula (I) was, e.g., esterified or amidated (e.g., compounds in which the carboxyl of the compound represented by formula (I) was ethyl-esterified, phenylesterified, phenylethylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, methyl amidated, alkylsulfonylamidated (e.g., —$CONHSO_2CH_3$ etc.) or arylsulfonylamidated (e.g., —$CONHSO_2Ph$ etc.)) when the compound represented by formula (I) has carboxy(s). These compounds may be produced by known method. The prodrug of the compound represented by formula (I) may be either a hydrate or a non-hydrate.

Further, the prodrug of the compound represented by formula (I) may change into the compound represented by formula (I) in physiological condition described in "The development of drug", Vol. 7, "molecular design", p. 163-198 (1990), Hirokawa shoten. Further, the compound represented by formula (I) may be labeled by an isotope (e.g., $^3H$, $^{14}C$, $^{35}S$ and $^{125}I$, etc.) etc.

The compound of the present invention represented by formula (I), salt thereof, solvate thereof or prodrug thereof (hereafter, it may be abbreviated to the compound of the present invention.) is a compound that excels in solubility, absorptivity and metabolic stability and has long-acting pharmacological activity (BLT2 binding activity), and further is weak in inhibition of drug metabolizing enzyme and circulatory toxicity. These properties are most important physical, pharmacological and chemical properties that are demanded when developing as a medicine and the compound of the present invention has the possibility to become a very excellent medicine that meets these requirements (The Merck Manual of Diagnosis and Therapy (17th Ed.), Merck & Co.).

The compound of the present invention can be evaluated to be useful as a medicine by various experimental systems, methods described in biological examples and appropriate improved methods thereof as follows. Further, the compound of the present invention can be evaluated to be excellent in dynamics, e.g., half-life in blood, stability in gut, oral absorptivity and bioavailability by known methods, e.g., methods described in "drug bioavailability (science of evaluation and improvement)", Jul. 6, 1998, gendai-iryousya. The compound of the present invention is named by ACD/NAME™, which is a computer program to mechanically generate IUPAC name, of Advanced Chemistry Development company. For example, the following compound was named sodium 3'-{[4-methoxybenzoyl(4-phenylbutyl)amino]methyl} 1,1'-biphenyl-3-carboxylate.

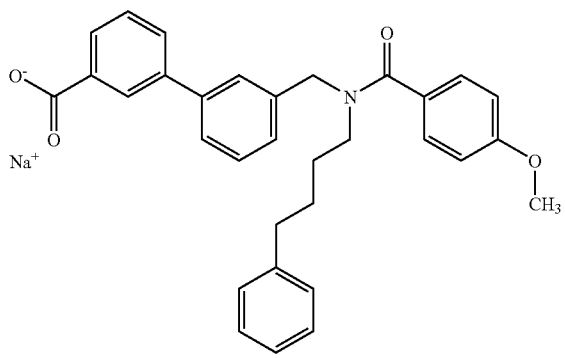 [SMILES: [Na+] ; COc1ccc(C(=O)N(CCCCc2ccccc2)Cc2cccc(-c3cccc(C(=O)[O-])c3)c2)cc1]

Process for Production of the Compounds of the Present Invention

The compound of the present invention is known as itself and can be produced by known methods, e.g., EP0632008, WO99/58513, WO00/48982, WO03/051852, and WO03/097851, etc., the method described in Comprehensive Organic Transformations: A Guide to Functional Group Preparations, 2nd Edition (Richard C. Larock, John Wiley & Sons Inc, 1999), the appropriate improved methods and the combined methods.

As a example of concrete production methods, the production method of the compound represented by formula (I-1) is described as follows.

The compound represented by formula (I-1) can be produced by subjecting the compound represented by formula (II)

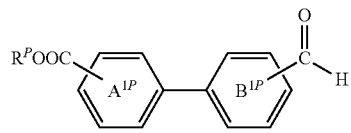

(wherein, ring $A^{1P}$ and ring $B^{1P}$ represent the same meaning as ring $A^1$ and ring $B^2$ respectively, and $R^P$ represents a protecting group of carboxyl group. However, carboxyl, hydroxyl, amino and thiol group contained in a group represented by ring A and ring B are protected if necessary and other symbols have the same meanings as defined above.) and the compound represented by formula (III)

$$R^{1P}-NH-R^{2P} \qquad (III)$$

(wherein, $R^{1P}$ and $R^{1P}$ represent the same meaning as $R^1$ and $R^2$ respectively. However, carboxyl, hydroxyl, amino and thiol group contained in a group represented by $R^{1P}$ and $R^{2P}$ are protected if necessary and other symbols have the same meanings as defined above.) to the reductive amidation reaction, followed by subjecting to deprotection, if necessary.

The reductive amination reaction is well-known and carried out at 0-40□, e.g., in an organic solvent (e.g., dichloroethane, dichloromethane, dimethylformamide, acetate or the mixture, etc.) in the existence of a reducing agent (e.g., sodium triacetoxyborohydride, sodium cyanoborohydride, sodium borohydride or tetrabutylammonium borohydride, etc.).

As be easily predictable for a person skilled in the art, the aimed compound of the present invention may be prepared by continuously subjecting to the deprotection reaction after appropriately protecting the groups in advance and subjecting to reaction.

The protective group of the amino includes, e.g., benzyloxycarbonyl, tert-butoxycarbonyl, allyloxycarbonyl(Alloc), 1-methyl-1-(4-biphenyl)ethoxycarbonyl(Bpoc), trifluoroacetyl, 9-fluorenylmethoxycarbonyl, benzyl(Bn), p-methoxybenzyl, benzyloxymethyl(BOM) and 2-(trimethylsilyl)ethoxymethyl(SEM), etc.

The protective group for the hydroxyl includes, e.g., methyl, trityl, methoxymethyl(MOM), 1-ethoxyethyl(EE), methoxyethoxymethyl(MEM), 2-tetrahydropyranyl(THP), trimethylsilyl(TMS), triethylsilyl(TES), tert-butyldimethylsilyl(TBDMS), tert-butyldiphenylsilyl(TBDPS), acetyl(Ac), pivaloyl, benzoyl, benzyl(Bn), p-methoxybenzyl, allyloxycarbonyl(Alloc) and 2,2,2-trichloroethoxycarbonyl(Troc).

The protective group of the mercapto includes, e.g., benzyl, methoxybenzyl, methoxymethyl(MOM), 2-tetrahydropyranyl(THP), diphenylmethyl and acetyl(Ac), etc.

The protective group of the carboxyl group includes, e.g., methyl, ethyl, tert-butyl, aryl, phenacyl and benzyl, etc.

The protective group of the carboxyl, hydroxyl, amino or thiol is not limited to the above protective group so far as it is a group which can be easily and selectively detached. For example, a deprotection reaction may be carried out by a method described in "T. W. Greene, Protective Groups in Organic Synthesis, Wiley, New York, 1999".

The deprotection reaction for the protective group of the carboxyl, hydroxyl, amino, or mercapto is known and includes, e.g., (1) alkaline hydrolysis;
(2) a deprotection reaction under acidic conditions;
(3) a deprotection reaction by hydrogenolysis;
(4) a deprotection reaction using metal complex;0
(5) a deprotection reaction using metal; and
(6) a deprotection reaction of silyl group.

These methods are specifically illustrated;
(1) The deprotection reaction by alkaline hydrolysis is carried out, e.g., using hydroxide of alkaline metal (e.g., sodium hydroxide, potassium hydroxide or lithium hydroxide, etc.), hydroxide of alkaline earth metal (e.g., barium hydroxide or calcium hydroxide, etc.), carbonate (e.g., sodium carbonate or potassium carbonate, etc.), the aqueous solution or the mixture in an organic solvent (e.g., methanol, tetrahydrofuran or dioxane, etc.) at 0 to 40° C.
(2) The deprotection reaction under acidic condition (e.g., deprotection reaction of tert-butoxycarbonyl or trityl, etc.) is carried out, e.g., in water or an organic solvent (e.g., dichloromethane, chloroform, 1,4-dioxane, ethyl acetate or anisole, etc.), inorganic acid (e.g., hydrochloric acid or sulfuric acid, etc.), or the mixture (e.g., hydrogen bromide/acetic acid) at 0 to 100° C.
(3) The deprotection reaction by hydrogenolysis (e.g., deprotection reaction of benzyl, benzhydryl, benzyloxycarbonyl or allyloxycarbonyl group, etc.) is carried out, e.g., in a solvent (e.g., ethers (e.g., tetrahydrofuran, dioxane, dimethoxyethane or diethyl ether, etc.), alcohol (e.g., methanol or ethanol etc.), benzene (e.g., benzene or toluene etc.), ketone (e.g., acetone or methylethylketone, etc.), nitrile (e.g., acetonitrile etc.), amide (e.g., dimethylformamide etc.), water, ethyl acetate or acetic acid, or the mixed solvent composed of two or more kinds.), in hydrogen atmosphere of ordinary pressure or high pressure or in the presence of ammonium formate, in the presence of a catalyst (e.g., palladium-carbon, palladium black, palladium hydroxide, platinum hydroxide, platinum oxide or raney nickel, etc.), at 0 to 200° C.
(4) The deprotection reaction using a metal complex (e.g., a deprotection reaction of allyloxycarbonyl group etc.) is carried out, e.g., using a metal complex (e.g., tetrakistriphenylphosphine palladium (0), bis(triphenylphosphine)palladium (II) dichloride, palladium (II) acetate or tris(triphenylphosphine) rhodium (1) chloride), in the presence or absence of a phosphine agent (e.g., triphenyl phosphine etc.), in the presence of a trap reagent (e.g., tributyltin hydride, triethylsilane, dimedone, morpholine, diethylamine or pyrrolidine, etc.), an organic acid (e.g., acetic acid, formic acid or 2-ethylhexanoic acid, etc.) and/or an organic acid salt (e.g., sodium 2-ethylhexanoate or potassium 2-ethylhexanoate, etc.), in an organic solvent (e.g., dichloromethane, dimethylformamide, tetrahydrofuran, ethyl acetate, acetonitrile, dioxane or ethanol, etc.), water or the mixed solvent at 0 to 40° C.
(5) The deprotection reaction using metal is carried out, e.g., in an acidic solvent (e.g., acetic acid, a buffer of pH 4.2 to 7.2 or a mixed solution of a solution thereof with an organic solvent such as tetrahydrofuran etc.), with ultrasonic wave if necessary, in the presence of powdery zinc, at 0 to 40° C.
(6) The deprotection reaction of silyl is carried out, e.g., using tetrabutylammonium fluoride, in an organic solvent miscible with water (e.g., tetrahydrofuran or acetonitrile, etc.) at 0 to 40° C.

As a person skilled in the art can easily understand it, the aimed compound of the present invention can be easily produced by using these deprotection reactions properly.

Among the compounds represented by formula (I-1), a compound that $R^1$ is represented by

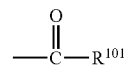

(wherein, $R^{101}$ represents a hydrocarbon group containing hydrogen(s) or substituent(s).), that is, a compound represented by formula (I-1a)

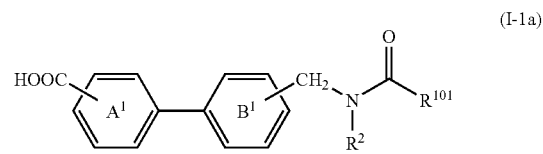

(I-1a)

(wherein, all symbols have the same meanings as defined above.) may be prepared by subjecting a compound represented by formula (IV)

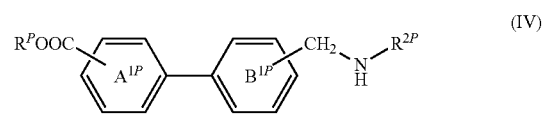

(IV)

(wherein, all symbols have the same meanings as defined above. However, carboxyl, hydroxyl, amino and thiol in a group represented by $R^{2P}$ are optionally protected and other symbols have the same meanings as defined above.) and a compound represented by formula (V)

HOOC—$R^{101P}$ (V)

(wherein, $R^{101P}$ has the same meaning as $R^{101}$, other symbols have the same meanings as defined above. However, carboxyl, hydroxyl, amino and thiol contained in a group represented by $R^{101P}$ are optionally protected.) to the amidation reaction and optionally subjecting to the deprotection reaction.

The amidation reaction has been known and includes, e.g.,
(1) a process using an acid halide,
(2) a process using a mixed acid anhydride and
(3) a process using a condensing agent.

These methods are specifically illustrated;
(1) The process using an acid halide is carried out, e.g., by reacting carboxylic acid with an acid halide (e.g., oxalyl chloride or thionyl chloride, etc.) in an organic solvent (e.g., chloroform, dichloromethane, diethyl ether, tetrahydrofuran, dimethoxyethane or toluene, etc.) or without solvent at −20° C. to refluxing temperature and reacting the resulting acid halide with an amine in the presence of a base (e.g., pyridine, triethylamine, dimethylaniline, dimethylaminopyridine or diisopropylethylamine, etc.) in an organic solvent (e.g., chloroform, dichloromethane, diethyl ether or tetrahydrofuran, etc.) at 0 to 40° C. The reaction can be also carried by reacting the resulting acid halide with an amine in an organic solvent (e.g., dioxane or tetrahydrofuran, etc.) using an alkali solution (e.g., sodium bicarbonate solution or sodium hydroxide solution, etc.) at 0 to 40° C.
(2) The process using a mixed acid anhydride is carried out, e.g., by reacting carboxylic acid with an acid halide (e.g., pivaloyl chloride, tosyl chloride or mesyl chloride, etc.) or an acid derivative (e.g., ethyl chloroformate or isobutyl chloroformate, etc.) in the presence of an organic solvent (e.g., chloroform, dichloromethane, diethyl ether or tetrahydrofuran, etc.) or without a solvent in the presence of a base (e.g., pyridine, triethylamine, dimethylaniline, dimethylaminopyridine or diisopropylethylamine, etc.) at 0 to 40° C. and reacting the resulting mixed acid anhydride with an amine in an organic solvent (e.g., chloroform, dichloromethane, diethyl ether or tetrahydrofuran, etc.) at 0 to 40° C.

(3) The process using a condensing agent is carried out, e.g., by reacting carboxylic acid with an amine using a condensing agent (e.g., 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide and 1-propylphosphonic acid cyclic anhydride; PPA, etc.), with or without 1-hydroxybenztriazole (HOBt), in the presence or absence of a base (e.g., pyridine, triethylamine, dimethylanilin or dimethylaminopyridine, etc.), in an organic solvent (e.g., chloroform, dichloromethane, dimethylformamide, diethyl ether or tetrahydrofuran, etc.) or without a solvent at 0 to 40° C.

The deprotection reaction of the protecting group can be carried by the same method above.

It is preferable that all of (1), (2) and (3) reactions are carried out in the water free condition under the inert gas atmosphere (e.g., argon or nitrogen, etc.).

The compounds represented by formula (II), (III), (IV) or (V) used as starting materials have been known as itself or can be easily produced by known methods, e.g., the method described in "Comprehensive Organic Transformations: A Guide to Functional Group Preparations 2nd Edition (Richard C. Larock, John Wiley & Sons Inc, 1999)", the appropriate improved methods and the combined methods.

For example, the compound represented by formula (II) can be produced by subjecting a compound represented by formula (VII)

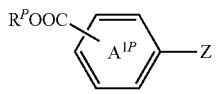

(VI)

(wherein, Z represents a halogen atom or triflate and other symbols have the same meanings as those defined above.) and a compound represented by formula (VII)

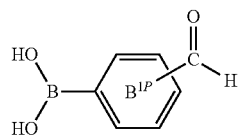

(VII)

(wherein, all symbols have the same meanings as those defined above.) to the following reaction.

This reaction is known and carried out at room temperature to 120° C., e.g., in a base (e.g., sodium ethylate, sodium hydroxide, potassium hydroxide, triethylamine, sodium carbonate, sodium hydrogencarbonate, potassium carbonate, cesium carbonate, thallium carbonate, potassium phosphate tribasic, cesium fluoride, barium hydroxide or tetrabutylammonium fluoride, etc.), the solution or the mixture and catalyst (e.g., tetrakis(triphenylphosphine)palladium(Pd (PPh$_3$)$_4$), bis dichloride(triphenylphosphine)palladium (PdCl$_2$(PPh$_3$)$_2$), palladium acetate(Pd(OAc)$_2$), palladium black, 1,1'-bis(diphenylphosphinoferrocene)dichloropalladium(PdCl$_2$(dppf)$_2$), diallyl palladium dichloride(PdCl$_2$(allyl)$_2$), or bis(triphenylphosphine)palladium iodide(PhPdI (PPh$_3$)$_2$), etc.) in an organic solvent (e.g., benzene, toluene, dimethylformamide, dioxane, tetrahydrofuran, methanol, acetonitrile, dimethoxyethane or acetone, etc.).

As be known by the persons skilled in the art, a reaction with heating in each reaction in the present specification may be carried out by using bathe, oil bath, sand bath or microwave.

In each reaction in the present specification, solid-supported reagents supported on high molecule polymer (e.g., polystyrene, polyacrylamide, polypropylene or polyethylene glycol etc.) may be properly used.

In each reaction described in the present specification, the reaction product can be purified by conventional purification techniques, e.g., distillation under atmospheric or reduced pressure, high performance liquid chromatography, thin-layer chromatography or column chromatography using silica gel or magnesium silicate, washing or recrystallization etc. The purification can be carried out for each reaction or after some reactions.

Toxicity

The toxicities of the compounds of the present invention are very low so that they are sufficiently safe for using as pharmaceuticals.

Application to Medicine

The compounds of present invention have BLT2 binding activities. On the other hand, since BLT2 most strongly is expressed to spleen and lymphocyte and is ubiquitous in a lot of organs including liver and ovary and further is highly expressed in keratinocyte and small intestine, in mammal (e.g., human, non-human animal, e.g., monkey, sheep, bovine, horse, dog, cat, rabbit, rat, and mouse, etc.), the compounds are useful for prevention and/or treatment of BLT2 mediated diseases, e.g., dermatosis [e.g., eczema, cheloma, lupus accompanied by skin injury, acne (e.g., acne vulgaris etc.), dermatitis (e.g., seborrheic dermatitis, solar dermatitis, contact dermatitis and atopic dermatitis, etc.), psoriasis (e.g., psoriasis vulgaris, guttate psoriasis, pustular psoriasis, arthropathic psoriasis, psoriatic erythroderma, etc.), keratosis (e.g., seborrheic keratosis, senile keratosis, actinic keratosis, photic keratosis and follicular keratosis, etc.), wart (e.g., condyloma, pointed condyloma, venereal wart, wart virus, molluscum contagiosum, leukoplakia and wart with human papillomavirus (HPV) infection such as vesicobullous lichen planus, etc.), skin cancer (e.g., rodent cancer, skin T lymphoma and local benign epidermosis (e.g., keratoderma and hard nevus, etc.), etc.), alopecic (e.g., congenital alopecia (e.g., diffuse congenital alopecia and congenital triangular alopecia, etc.), acquired alopecia (folliculitis decalvans, alopecia greata and follicular mucinosis, etc.), etc.), dyspigmentation (e.g., stain, freckle and suntan, etc.), etc.], intestinal disease (e.g., inflammatory intestinal disease (e.g., inflammatory bowel disease and Crohn's disease, etc.), irritable bowel syndrome and colitis, etc.), HIV infection, acquired immunodeficiency syndrome, rejection to transplant, transplant rejection, graft-versus-host disease, autoimmune disease (e.g., systemic erythematodes, rheumathritis, myasthenia gravis and multiple sclerosis, etc.), allergic disease (e.g., atopic dermatitis and bronchial asthma, etc.), inflammation, infection, ulcers, lymphoma, malignant tumor, leucaemia, arterial sclerosis, hepatitis, hepatic cirrhosis or cancer, etc.

The compound of the present invention may be administered as a combined preparation by combining with other pharmaceutical(s) for the purpose of;
1) the supplementing and/or enhancing of the prevention and/or treatment effect of the compound of the present invention,
2) the improvement in pharmacokinetics and absorption and the dose reduction of the compound of the present invention and/or
3) the side effect reduction of the compound of the present invention.

As a concomitant use of the compound of the present invention and other pharmaceutical, a blending pharmaceutical in which both components are compounded in a preparation may be administered or separate preparations may be administered. The administration of separate preparations includes a simultaneous administration and administrations with time difference. In the administration with time difference, the compound of the present invention may be firstly administered followed by administering the other pharmaceutical or the other pharmaceutical may be firstly administered followed by administering the compound of the present invention. Each administration method may be same or different.

The other pharmaceutical may be a low molecular weight compound, protein, polypeptide, polynucleotide (DNA, RNA or gene), antisense, decoy, antibody or vaccine, etc. A dosage of the other pharmaceutical can be properly selected on the basis of the clinical dose. Further, a mix proportion of the other pharmaceutical and the compound of the present invention can be properly selected on the basis of age and weight of a subject, medication method, administration period, disease, symptom or combination, etc. For example, 0.01 to 100 of the other pharmaceutical for a mass of the compound of the present invention may be used. Two or more arbitrary other pharmaceuticals may be combinationally administered at a suitable proportion.

The other preventive and/or therapeutic pharmaceutical(s), which is/are combined with the compound of the present invention, for dermatosis such as eczema, cheloma, lupus accompanied by skin injury, acne (e.g., acne vulgaris etc.), dermatitis (e.g., seborrheic dermatitis, solar dermatitis, contact dermatitis and atopic dermatitis, etc.), psoriasis (e.g., psoriasis vulgaris, guttate psoriasis, pustular psoriasis, arthropathic psoriasis, and psoriatic erythroderma, etc.), keratosis (e.g., seborrheic keratosis, senile keratosis, actinic keratosis, photic keratosis and follicular keratosis, etc.), wart (e.g., condyloma, pointed condyloma, venereal wart, wart virus, molluscum contagiosum, leukoplakia and wart with human papillomavirus (HPV) infection such as vesicobullous lichen planus, etc.) and skin cancer (e.g., rodent cancer, skin T lymphoma and local benign epidermosis (e.g., keratoderma and hard nevus, etc.), etc.) include(s), e.g., SH-enzyme activator (e.g., L-cysteine etc.), aminoglycoside antibiotic (e.g., gentamicin sulfate etc.), allergic disease agent (olopatadine hydrochloride, cyproheptadine hydrochloride, fexofenadine hydrochloride, bepotastine besilate, tranilast, epinastine hydrochloride, olopatadine hydrochloride, olopatadine hydrochloride, cyproheptadine hydrochloride, fexofenadine hydrochloride, oxatomide, emedastine fumarate, ketotifen fumarate, bepotastine besilate, azelastine hydrochloride, Isothipendyl hydrochloride, epinastine hydrochloride, olopatadine hydrochloride, cyproheptadine hydrochloride, fexofenadine hydrochloride, oxatomide, sodium cromoglycate, suplatast tosilate, tranilast, emedastine fumarate, ketotifen fumarate and bepotastine besilate, etc.), ampicillin-sulbactam mutual prodrug (e.g., sultamicillin tosilate etc.), imidazole fungicide (e.g., ketoconazole etc.), imidazole antiulcer anti-inflammatory drug (e.g., bendazac etc.), calcium preparation (e.g., calcium hydroxide etc.), cephalosporin antibiotics (e.g., cefalexin and cefuroxime axetil, etc.), cephem antibiotics (e.g., cefotiam hexetil hydrochloride, cefadroxil and cefpodoxime proxetil, etc.), tetracycline antibiotics (e.g., doxycycline hydrochloride and minocycline hydrochloride, etc.), acne drug (e.g, pregnanediol etc.), new quinolone antimicrobial drug (e.g., enoxacin, lomefloxacin hydrochloride, ofloxacin, ciprofloxacin, sparfloxacin, tosufloxacin tosilate, nadifloxacin, norfloxacin, fleroxacin, levofloxacin and enoxacin, etc.), pantothenate drug (e.g., pancal granules etc.), vitamin A (e.g., retinol palmitate and vitamin A, etc.), riboflavins (e.g., riboflavin, riboflavin sodium phosphate, and butyric acid riboflavin, etc.), vitamin B2/B6 (e.g., riboflavin pyridoxine hydrochloride etc.), vitamin B6 (e.g., pyridoxine hydrochloride etc.), vitamin C (e.g., ascorbic acid etc.), vitamin E/A (e.g., tocopherol vitamin A oil etc.), vitamin H (e.g., biotin etc.), phenylpropionic acid antiphlogistic sedative drug (e.g., suprofen and Ibuprofenpiconol, etc.), phenothiazine antihistaminic (e.g., alimemazine tararate and mequitazine, etc.), proprionic acid antiphlogistic-sedative-drug (e.g., ketoprofen etc.), penem antibiotics (e.g., faropenem sodium etc.), benzhydryl ether antihistaminic (e.g., clemastine fumarate etc.), macrolide antibiotics (e.g., erythromycin, clarithromycin, josamycin and rokitamycin, etc.), lincomycin antibiotics (e.g., clindamycin etc.), pharmaceutical gas (e.g., carbon dioxide etc.), vesicant (e.g., cantharidis tincture etc.), antipyretic analgesics (e.g., aluminium flufenamate etc.), dermatologic (e.g., sulfur and camphor etc.), keratosis drug (e.g., urea etc.), aromatic tetraene derivative for keratosis (e.g., etretinate etc.), keratin softening and anti-trichophytia medicine (e.g., salicylic acid etc.), active vitamin D3 keratosis and psoriasis vulgaris drug (e.g., tacalcitol etc.), chinese medicine (e.g., syohusan, zyumi-haidokuto, toki-syakuyaku-san, makyo-kansekito, unkeitou, eppika-zyututo, kakkonto, kami-shoyo-san, keisi-bukuryogan, saiko-seikanto, syohusan, sinbuto, zyami-haidokuto, daio-botanpito, jizusoippo, tokaku-zyokito, tokiinshi, hatimi-ziogan, bohutusyo-san, ryutan-syakanto and syouma-kakkontou, etc.), drug for liver disease and allergy (e.g., glycyron etc.), drug for hepatopathy and antiallergic drug (e.g., stronger neo-minophagen C etc.), drug for parasitic dermatosis (e.g., sulfur etc.), bronchodilator and antitussive drug (e.g., dl-methylephedrine hydrochloride etc.), topical astringent (e.g., calamine etc.), anticoagulant drug (e.g., heparin sodium etc.), blood component preparation (e.g., hydroxyzine pamoate and hydroxyzine hydrochloride, etc.), antihistamine drug (e.g., diphenhydramine, diphenhydramine tannate, diphenylpyraline chlorotheophyllinate, chlorpheniramine maleate, diphenhydramine laurylsulfate, diphenhydramine hydrochloride and triprolidine hydrochloride, etc.), antibradykinin antihistaminic drug (e.g., homochlorcyclizine hydrochloride etc.), antiplasmin agent (e.g., epsilon-aminocaproic acid and tranexamic acid, etc.), antipellagra factor (e.g., nicotine acid and nicotinamide, etc.), anti-inflammatory hematogenous promoter and moisturizing agent (e.g., heparinoid etc.), antifingal and anti-inflammatory hemorrhoidal preparation (e.g., proctosedyl etc.), antitumor antibiotics (e.g., bleomycin hydrochloride and peplomycin sulfate, etc.), antibiotics (e.g., fusidate sodium etc.), antibiotic agent (e.g., chlomy-P etc.), semisynthetic penicillin (e.g., amoxicillin and lenampicillin hydrochloride, etc.), antiseptic disinfectants (e.g., resorcine etc.), acid-stable macrolide antibiotics (e.g., roxithromycin etc.), persistent selective H1-receptor antagonist and antiallergic drug (e.g., lolatadine etc.), persistent selective H1-receptor antagonist (e.g., ebastine and cetirizine hydrochloride, etc.), hemorrhoidal preparation (e.g., *E. coli* killed bacteria and hydrocortisone etc.), antiinflammatory and analgetic drug (e.g., ufenamate etc.), antiinflammatory drug (e.g., azulene etc.), neural immunoregulating, paregoric, calmative and antiallergic drug (e.g., vaccinia virus inoculable rabbit inflammatory dermal extract etc.), drug for psoriasis vulgaris (e.g., calcipotriol etc.), agent for biological oxidation-reduction balance (e.g., glutathione etc.), dysbolism improving drug (e.g., pantethine, panthenol and calcium pantothenate, etc.), antipruritic, astringent and antiinflammatory drug (e.g., zinc oxide and salicylic acid etc.), antipruritic and antiinflammatory drug (e.g., hydrocortisone crotamiton etc.), antipruritic drug (e.g., crotamiton etc.), drug for keratosis such as secondary hyperparathyreosis and psoriasis vulgaris (e.g., maxacalcitol etc.), skin fester drug (e.g., acrinol and zinc oxide oil etc.), drug for dermatosis and Hansen's disease (e.g., diaphenylsulfone etc.), external drug for dermatosis (e.g., pine tar, aluminum chlorohydroxyallantoinate, eksalb, dexamethasone and defatted soybean retorted tar, defatted soybean retorted tar and diphenhydramine and combined DM, etc.), emollient (e.g., glycerin and potash solution etc.), nonsteroidal anti-inflammatory drug (e.g., bufexamac and glycyrrhetic acid, etc.), adrenocorticosteroid (e.g., amcinonide, eurich, kenacort-AG, hydrocortisone sodium succinate, dexamethasone, triamcinolone, triamcinolone acetonide, halcinonide, hydrocortisone, flumetasone pivalate, mometasonei Furoate, fluocinonide, fluocinolone acetonide, fludroxycortide, prednisolone, aoclometasone dipropionate, clobetasol propionate, dexamethasone propionate, deprodone propionate, beclometasone dipropionate, betamethasone, dexamethasone sodium metasulfobenzoate, methylprednisolone, dexamethasone sodium phosphate, betamethasone sodium phosphate, diflucortolone valerate, dexamethaxone valerate, betamethasone valerate, prednisolone valerate acetate, cortisone acetate, diflorazone diacetate, dexamethasone acetate, paramethasone acetate, hydrocortisone acetate, betamethasone acetate and phosphate betamethasone sodium, methylprednisolone acetate, prednisolone sodium succinate for injection, clobetasone butyrate, hydrocortisone butyrate, hydrocortisone butyrate propionate and betamethasone butyrate propionate, etc.), adrenocorticosteroid and antibiotics combination drug (e.g., oxytetracycline hydrochloride and hydrocortisone, tetracycline hydrochloride and hydrocortisone acetate, batamethasone valerate and gentamicin sulfate, fradiomycine sulfate and fluocinolone acetonide, fradiomycine sulfate and prednisolone, fradiomycine sulfate and methylprednisolone, fradiomycine sulfate and betamethasone sodium phosphate, fradiomycine sulfate and betamethasone valerate, etc.), adrenocorticosteroid combination drug (e.g., betamethasone and dexchlorpheniramine maleate etc.), vitamin complex (e.g., Wasser-V etc.), complex antibiotic agent (e.g., colistine sulfate and fradiomycine sulfate, etc.), coenzyme vitamin B2 (e.g., flavine adenine dinucleotide etc.), vitamin B2/B6 preparation (e.g., flavin adenin dinucleotide sodium and pyridoxal phosphate, etc.), coenzyme vitamin B6 (e.g., pyridoxal phosphate etc.), immunosuppressive and atopic dermatitis drug (e.g., tacrolimus hydrate etc.) and immunosuppressive drug (e.g., cyclosporine etc.).

The other preventive and/or therapeutic pharmaceutical(s), which is/are combined with the compound of the present invention, for alopecic (e.g., congenital alopecia (e.g., diffuse congenital alopecia and congenital triangular alopecia, etc.), acquired alopecia (folliculitis decalvans, alopecia greata and follicular mucinosis, etc.), etc.) and dyspigmentation (e.g., stain, freckle and suntan, etc.), etc. include(s), e.g., vitamin C (e.g., ascorbate etc.), vitamin C preparation (e.g., ascorbate and calcium pantothenate, etc.), chinese medicine (e.g., keisika-ryukotu-boreito etc.), drug for liver disease and allergy (e.g., glycyron etc.), antiseptic disinfectants (e.g., resorcine etc.), agent for biological oxidation-reduction balance (e.g., glutathione etc.), epilatory and effusion and hypoleukocytosis inhibitor (e.g., cepharanthin etc.), parasympathomimetic drug (e.g., acetylcholine chloride etc.), parasympathetic nerve stimulator (e.g., carpronium chloride etc.) and adrenocorticosteroid (e.g., amcinonide, difluprednate, betamethasone dipropionate, dexamethasone, triamcinolone, triamcinolone acetonide, hydrocortisone, mometasone furoate, fluocinonide, prednisolone, clobetasol propionate, dexamethasone propionate, deprodone propionate, methylprednisolone, phosphate dexamethasone sodium, phosphate betamethasone sodium, betamethasone valerate, diflorazone diacetate and phosphate betamethasone sodium, methylprednisolone acetate, prednisolone sodium succinate for injection and hydrocortisone butyrate propionate, etc.), etc.).

The other preventive and/or therapeutic pharmaceutical(s), which is/are combined with the compound of the present invention, for autoimmune disease include(s), e.g., nonsteroidal anti-inflammatory drug (e.g., sasapyrine, sodium salicylate, aspirin, aspirin/dialuminate, diflunisal, indometacin, suprofen, ufenamate, dimethyl isopropyl azulene, bufexamac, felbinac, diclofenac, tolmetin sodium, clinoril, fenbufen, napument, puroglumetacine, indomethacin farnesyl, acemetacin, proglumetacin maleate, amfenac sodium, mofebutazone, etodolac, ibuprofen, ibuprofenpiconol, naproxen, flurbiprofen, flurbiprofen axetil, ketoprofen, calcium fenprofen, tiaprofen, oxaprozin, pranoprofen, loxoprofen sodium, aluminoprophen, zaltoprofen, mefenamic acid, alminum mefenamete, glycyrrhetic acid, tolfenamic acid, floctafenine, ketophenylbutaaone, oxyphenbutazone, piroxicam, tenoxicam, ampiroxicam, napageln ointment, epirizole, tiaramide hydrochloride, tinoridine hydrochloride, emorfazone, sulpyrine, migrenin, saridon, sedes-G, amipylo-N, sorbon, pyrine medicine, acetaminophen, phenacetin, dimetotiazine mesilate, simetride combination drug and non-pyrine medicine, etc.), disease modifying anti-rheumatic drug (DMARDs and delayed anti-rheumatic drug) (e.g., aurothioglucose, sodium aurothiomalate, auranofin, actarit, D-penicillamine preparation, lobenzarit disodium, bucillamine, hydroxychloroquine, salazosulfapyridine, methotrexate and leflunomide, etc.), adrenocorticosteroid (e.g., as a drug for external use, clobetasol propionate, diflorazone diacetate, fluocinonide, mometasone furoate, betamethasone dipropionate, hydrocortisone butyrate propionate, batamethasone valerate, difluprednate, pudesonide, diflucortolone valerate, amcinonide, halcinonide, dexamethasone, dexamethasone propionate, dexamethason valerate, dexamethasone acetate, hydrocortisone acetate, hydrocortisone butyrate, hydrocortisone butyrate propionate, deprodone propionate, prednisolone valerate acetate, fluocinolone acetonide, beclometasone dipropionate, triamcinolone acetonide, flumetasone pivalate, alclometasone dipropionate, clobetasone butyrate, prednisolone, beclometasone dipropionate and fludroxycortide, etc., as an internal medicine and an injection, cortisone acetate, hydrocortisone, phosphate hydrocortisone sodium, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone diacetate, dexamethasone, dexamethasone acetate, dexamethasone sodium phosphate, dexamethasone palmitate, paramethasone acetate and betamethasone, etc., as an inhalant, beclometasone dipropionate, fluticasone propionate, budesonide, flunisolide, triamcinolone, ST-126P, ciclesonide, dexamethasone palomithionate, mometasone furoate, prasterone sulfonate, deflazacort, methylprednisolone threbutanate, and methylprednisolone sodium succinate, etc.), immunosuppressive drug (e.g., tacrolimus (FK506), cyclosporine, sirolimus (rapamycin), corticosteroid, azathiopurine, mycophenolate mofetil, cyclophosphamide, etc.), antiphlogistic enzyme (e.g., lysozyme chloride, bromelain, pronase, serrapeptase, streptokinase and streptodornase combination drug, etc.), cartilage protective (e.g., sodium hyaluronate, glucosamine, chondroitin sulfuric acid, glycosaminoglycan polysulfate inhibitor, etc.), T lymphocyte inhibitor, TNF-alpha inhibitor (e.g., infliximab, adalimumab and etanercept, etc.), prostaglandin synthase inhibitor (e.g., salazosulfapyridine, mesalazine, olsalazine, 4-aminosalicylic acid, JTE-522, auranofin, carprofen, diphenpiramide, flunoxaprofen, flurbiprofen, indomethacin, ketoprofen, lornoxicam, loxoprofen, meloxicam, oxaprozin, parsalmid, piproxen, piroxicam, piroxicam betadex, piroxicam cinnamate, tropineindomethacinate, zaltoprofen, pranoprofen, etc.), IL-6 inhibitor (e.g., MRA etc.), Interferon-gamma agonist, IL-1 inhibitor (e.g., anakinra etc.), EDG-1 agonist, EDG-6 agonist, prostaglandins (hereafler, it is abbreviated as PG.)(e.g., PG receptor agonist and PG receptor antagonist, etc. PG receptor includes PGE receptor (EP1, EP2, EP3 and EP4), PGD receptor (DP and CRTH2), PGF receptor (FP), PGI receptor (IP) and TX receptor (TP), etc.) and include(s) phosphodiesterase inhibitor (e.g., rolipram (PDE4 inhibitor), cilomilast (trade name Arifro), Bay19-8004, NIK-616, Roflumilast (BY-217), cipamphiline (BRL-61063), atizoram (CP-80633), SCH-351591, YM-976, V-11294A, PD-168787, D-4396, IC-485 and ONO-6126, etc.), metalloproteinase inhibitor, chemokine receptor antagonist (e.g., endogenous ligand of chemokine receptor (e.g., MIP-1α, MIP-1β, RANTES, SDF-1α, SDF-1β, MCP-1, MCP-2, MCP-4, Eotaxin and MDC, etc., or derivative thereof (e.g., AOP-RANTES, Met-SDF-1 alpha, and Met-SDF-1beta, etc.), and non-peptide low molecular weight compound (e.g., CCR2, CCR3, CCR4, CCR5, CXCR1, CXCR2, CXCR3 or CXCR4 receptor antagonist and agonist, etc.) or Chemokine receptor (e.g., Pro-140 etc.) and adhesive molecule inhibitor (e.g, antiIntegrin α 4 antibody, etc.), etc.

The other preventive and/or therapeutic pharmaceutical(s), which is/are combined with the compound of the present invention, for HIV infection and acquired immunological deficiency syndrome include(s), e.g., reverse transcriptase inhibitor, protease inhibitor, chemokine (e.g., CCR2, CCR3, CCR4, CCR5, CXCR1, CXCR2, CXCR3 or CXCR4) antagonist, fusion inhibitor, antibody for surface antigen of HIV-1 and HIV-1 vaccine, etc.

The other preventive and/or therapeutic pharmaceutical(s), which is/are combined with the compound of the present invention, for atopic dermatitis include(s), e.g., steroid, nonsteroidal antiflammatory drug, immunosuppressive drug, PGs, antiallergic drug, mediator release inhibitor, antihistaminic, forskolin preparation, phosphodiesterase inhibitor and cannabinoid-2 receptor stimulator, etc.

The other preventive and/or therapeutic pharmaceutical(s), which is/are combined with the compound of the present invention, for arteriosclerosis include(s), e.g., HMG-CoA reductase inhibitor, fibrate preparation, probucol preparation, anion exchange resin, EPA preparation, nicotinic acid preparation, MTP inhibitor, other anti-cholesterol drug and EDG-2 antagonist, etc.

The other preventive and/or therapeutic pharmaceutical(s), which is/are combined with the compound of the present invention, for Crohn's disease and ulceous colitis include(s), e.g., steroid, elastase inhibitor, cannabinoid-2 receptor stimulator, prostaglandins, prostaglandin synthase inhibitor, phosphodiesterase inhibitor, metalloproteinase inhibitor, adhesive molecule inhibitor, anti-cytokine protein preparation, anti-cytokine drug, immunomodulator, leukotriene receptor antagonist, antiparasympathoniietic drug, 5-lipoxygenase inhibitor, nitric oxide synthase (NOS) inhibitor, interleukin-8 antagonist, poly(ADP-ribose)polymerase (PARP) inhibitor, mitochondriaa benzodiazepine receptor (MBR) agonist, antioxidant, local anesthetic, antiulcer drug, protection factor promoter, mesalazine, salazosulfapyridine and TNF-alpha antagonist, etc.

The other preventive and/or therapeutic pharmaceutical(s), which is/are combined with the compound of the present invention, for irritable bowel syndrome include(s), e.g., anti-anxiety drug (e.g., benzodiazepine, thienodiazepin and non-benzodiazepine, etc.), antidepressant drug (e.g., monoamine releaser, monoamine oxidase (MAO) inhibitor, monoamine reuptake inhibitor (SNRI and SSRI), dopamine (D2) antagonist, CRF antagonist, Beta 3 agonist, neurotensin antagonist, NK1 antagonist, tricyclic antidepressant and tetracyclic antidepressant, etc.), antiparasympathomimetic drug, affinity polyacrylamide resin, antidiarrheal drug, mucosal paralyzant, bulk catharic, saline cathartic, fiber pharmaceutical, drug for controlling intestinal function, autonomic nerve modulator, calcium channel blocking agent, phosphodiesterase inhibitor, serotonin antagonist (e.g., 5-HT3 antagonist and 5-HT4 antagonist, etc.), serotonin agonist (e.g., 5-HT4 agonist and 5-HT1A agonist, etc.), digestive function modulator (e.g., CCK-A antagonist, NK1 antagonist, NK2 antagonist, 5-HT1A agonist, muscarinic agonist, 5-lipoxygenase inhibitor, CRF antagonist, etc.) and mitochondriaa benzodiazepine receptor (MBR) agonist, etc.

The other preventive and/or therapeutic pharmaceutical(s), which is/are combined with the compound of the present invention, for colitis include(s), e.g., steroid, nitric oxide synthase (NOS) inhibitor, prostaglandins, poly(ADP-ribose) polymerase (PARP) inhibitor, phosphodiesterase 4 inhibitor, elastase inhibitor, Interleukin-8 antagonist and cannabinoid-2 receptor stimulatior, etc.

Other pharmaceuticals supplementing and/or enhancing of the prevention and/or treatment effect of the compound of the present invention include not only one that was found so far but also one that will be found in the future.

There is no particular limitation for the diseases showing the prevention and/or treatment effect by the foregoing combined preparation, so far as it is a disease in which the prevention and/or treatment effect of the compound of present invention are supplemented and/or enhanced.

When the compound of the present invention or the combined preparation of the compound of the present invention and other pharmaceutical(s) is used for the foregoing purpose, it is systemically or topically administered in oral or parenteral form usually.

The dose varies depending upon age, body weight, symptom, therapeutic effect, administering method or treating time, etc. Generally, 100 μg to 1,000 mg per an adult is orally administered once to several times per a day, or 50 μg to 500 mg per an adult is parenterally administered one to several times per a day, or is continuously administered from vein for 1 to 24 hour(s) per a day.

Since the dose changes depending on various conditions as described above, there are cases in which doses lower than or greater than the above ranges may be used.

When the compound of the present invention or the combined preparation of the compound of the present invention and other pharmaceutical is administered, it is used as internal solid composition for oral administration, internal liquid composition and injection, external preparation, suppository, eye drop or inhalant, etc., for parenteral administration.

The internal solid composition for oral administration includes, e.g., tablets, pills, capsules, diluted powder and granules etc. The capsules include hard capsules and soft capsules.

In such a solid composition, one or more active substance(s) is used by itself or by being mixed with vehicle (e.g., lactose, mannitol, glucose, microcrystalline cellulose, and starch, etc.), binding agent (e.g., hydroxypropylcellulose, polyvinyl pyrrolidone, and magnesium aluminometasilicate, etc.), disintegrator (e.g., sodium carboxymethylcellulose etc.), lubricant (e.g., magnesium stearate etc.), stabilizer or solubilizer (e.g., glutamate and aspartic acid, etc.), etc., and being pharmaceutically manufactured by a conventional method. The solid composition may be coated with coating (e.g., saccharose, gelatin, hydroxypropylcellulose or hydroxypropylmethylcellulose phthalate, etc.), if necessary, or may be coated with two or more layers. Capsule of a substance that can be absorbed such as gelatin is also included.

The internal liquid composition for oral administration includes pharmaceutically acceptable solution, suspension, emulsum, syrup and elixir, etc. In the liquid composition, one or more active substance(s) is/are dissolved, suspended or emulsified in a commonly used inert diluent (e.g., pure water, ethanol or the mixture, etc.). The composition may contain moisturizer, suspending agent, sweetener, flavor, aromatic agent, preservative and buffer, etc.

The external preparation for parenteral administration includes, e.g., ointment, gel, cream, fomentation, patch, embrocation, nebula, inhalant, spray, aerosol, eye drop and nosedrop, etc. These may contain one or more activator(s) and may be prepared by known methods or conventional methods.

The ointment may be prepared by known methods or conventional methods. For example, it may be prepared by levigating and melting one or more activator(s) into a base. The ointment base is chosen from known or usually used ones. For example, it is used by mixing with one or more chosen from higher fatty acid or higher fatty acid ester (e.g., adipic acid, myristic acid, palmitic acid, stearic acid, oleic acid, adipic acid ester, myristic acid ester, palmitate, stearic acid ester or oleate, etc.), rows (e.g., beeswax, spermaceti wax or ceresin, etc.), surfactant (e.g., polyoxyethylene alkyl ether phosphate ester etc.), higher alcohol (e.g., cetanol, stearyl alcohol or cetostearyl alcohol, etc.), silicone oil (e.g., dimethylpolysiloxane etc.), hydrocarbons (e.g., hydrophilic petrolatum, white petrolatum, purified lanolin or liquid paraffin, etc.), glycols (e.g., ethylene glycol, diethylene glycol, propylene glycol, polyethylene glycol or macrogol, etc.), vegetable oil (e.g., castor oil, olive oil, sesame oil or turpentine oil, etc.), animal oil (e.g., mink oil, yolk oil, squalane or squalene, etc.), water, absorption promoter and poison inhibitor. Further, it may include moisturizing agent, preservative, stabilizing agent, anti-oxidant or flavor, etc.

The gel may be prepared by known methods or conventional methods. For example, it may be prepared by melting one or more activator(s) into a base. The gel base is chosen from known or usually used ones. For example, it is used by mixing with one or more base(s) chosen from lower alcohol (e.g., ethanol and isopropyl alcohol, etc.), gelatinizer (e.g., carboxymethylcellulose, hydroxyethylcellulose, hydroxypropylcellulose or ethylcellulose, etc.), neutralizer (e.g., triethanolamine or diisopropanolamine, etc.), surfactant (e.g., polyethylene glycol monostearate etc.), gums, water, absorption promoter and poisoned inhibitor. Further, it may include preservative, anti-oxidant or flavor, etc.

The cream is prepared by known methods or conventional methods. For example, it may be prepared or emulsified by melting one or more activator(s) into a base. The cream base is chosen from known or usually used ones. For example, it is used by mixing with one or more base(s) chosen from higher fatty acid ester, lower alcohol, hydrocarbons or polyhydric alcohol (e.g., three propyleneglycol or 1,3-butyleneglycol, etc.), higher alcohol (e.g., 2-hexyldecanol or cetanol, etc.) and emulsifier (e.g., polyoxyethylene alkyl ethers or fatty acid esters, etc.). Further, it may include preservative, anti-oxidant or flavor, etc.

The fomentation is prepared by known methods or conventional methods. For example, it may be prepared by melting one or more activator(s) into a base, followed by kneading, rolling and spreading on carrier. The fomentation base is chosen from known or usually used ones. For example, it is used by mixing with one or more base(s) chosen from thickener (e.g., polyacrylic acid, polyvinyl pyrrolidone, arabic gum, starch, gelatin or methylcellulose, etc.), penetrant (e.g., urea, glycerin or propyleneglycol, etc.), filler (e.g., china clay, zinc oxide, talc, calcium or magnesium, etc.), water, solubilizer, tackifier and poison inhibitor. Further, it may include preservative, anti-oxidant or flavor, etc.

The patch is prepared by known methods or conventional methods. For example, it may be prepared by melting one or more activator(s) into a base followed by rolling and spreading on carrier. The patch base is chosen from known or usually used ones. For example, it is used by mixing with one or more base(s) chosen from polymeric matrix, oils and fats, and higher fatty acid, tackifier and poison inhibitor. Further, it may include preservative, anti-oxidant or flavor, etc.

The liniment is prepared by known methods or conventional methods. For example, it may be prepared by dissolving, suspending or emulsifying one or more activater(s) into one or more base(s) chosen from water, alcohol (e.g., ethanol or polyethylene glycol, etc.), higher fatty acid, glycerin, soap, emulsifier and suspending agent, etc. Further, it may include preservative, anti-oxidant or flavor, etc.

The spray, the inhalant and the aerosol may contain a stabilizer such as sodium hydrogen sulfite or a buffer giving isotonicity, e.g., isotonizing agent such as sodium chloride, sodium citrate or citric acid, etc. A manufacturing method of spray is described, e.g., in U.S. Pat. Nos. 2,868,691 and 3,095,355 in detail.

The injection for parenteral administration includes all injections and the drip, too. It includes, e.g., muscle injection, hypodermic injection, intradermic injection, intra-arterial injection, intravenous injection, endoceliac injection, intrathecal injection and intravenous drip, etc.

The injection for parenteral administration includes solution, suspension, emulsion, and solid injection that is dissolved or suspended into a solvent before use. The injection may be used by dissolving, suspending or emulsifying one or more activator(s) into a solvent. For example, distilled water for injection, physiologic saline, vegetable oil, propylene glycol, polyethylene glycol or alcohols such as ethanols or combination thereof is used as a solvent. Further, the injection may include stabilizer, solubilizer (e.g., glutamic acid, glutamic acid and POLYSORBATE 80 (registered trade mark), etc.), glutamic acid, emulsifier, soothing agent, buffer and preservative, etc. These are sterilized in the final process or manufactured by the aseptic manipulation. Sterile solid compositions may also be used, e.g., by being freeze-dried and being aseptic or dissolved to aseptic distilled purified water or other solvents before use.

The eye drop for parenteral administration includes eye drops, eye drops of a suspension type, eye drops of an emulsion type, eye drops which is dissolved upon actual use, and eye ointment.

The eye drop may be manufactured according to a known method. For example, is/are used by being dissolving, suspending or emulsifying one or more activator(s) into a solvent. For example, sterile purified water, physiologic saline and other water solvents or injectable non-aqueous solvent (e.g., vegetable oil etc.), etc., and combination thereof is used as a solvent of the eye drop. The eye drop may appropriately contain isotonizing agent (e.g., sodium chloride or concentrated glycerol, etc.), buffering agent (e.g., sodium phosphate or sodium acetate, etc.), surfactant (e.g., Polysorbate 80 (trade name), polyoxyl stearate 40 or polyoxyethylene hydrogenated castor oil, etc.), stabilizer (e.g., sodium citrate or sodium edetate, etc.), antiseptic agent (e.g., benzalkonium chloride or paraben, etc.), if necessity. These are sterilized in the final process or manufactured by the aseptic manipulation. Sterile solid compositions may also be used, e.g., by being freeze-dried and being aseptic or dissolved to aseptic distilled purified water or other solvents before use.

The inhalation agent for parenteral administration includes aerosol preparation, powder for inhalation and liquid for inhalation. The liquid for inhalation may be such a form that the ingredient is dissolved or suspended in water or in other appropriate medium in actual use.

Those inhalation agents are prepared according to known methods.

For example, in the case of liquid for inhalation, antiseptic agent (benzalkonium chloride or paraben etc.), coloring agent, buffer (sodium phosphate or sodium acetate etc.), isotonizing agent (sodium chloride or concentrated glycerol etc.), thickener (carboxyvinyl polymer etc.) or absorption promoter, etc., are appropriately selected and prepared if necessary.

In the case of powder for inhalation, lubricant (stearic acid or salt thereof, etc.), binder (e.g., starch or dextrin, etc.), excipient (e.g., lactose or cellulose, etc.), coloring agent, antiseptic (e.g., benzalkonium chloride or paraben, etc.) or absorption promoter, etc., are appropriately selected and prepared if necessary.

In the administration of the liquid for inhalation, a spraying device (e.g., atomizer or nebulizer etc.) are usually used and in the administration of the powder for inhalation, an administering device for inhalation of powdery pharmaceutical is usually used.

Other composition for parenteral administration, which contains one or more activator(s), includes suppository for intrarectal administration and pessary for intravaginal administration, etc., which can be prepared by known methods.

Effect of the Invention (1) The compound having BLT2 binding activity, salt thereof, solvate thereof or prodrug thereof is useful for the prevention and/or therapy for skin disease.
(2) The compound of the present invention has BLT2 binding activity. Therefore, it is useful for the prevention and/or therapy for skin disease, intestinal disease, HIV infection, acquired immunological deficiency syndrome, rejection to transplant, transplant rejection, graft-versus-host disease, autoimmune disease, allergic disease, inflammation, infectious disease, ulcus, lymphoma, carcinoma, leukosis, arteriosclerotic, hepatitis or liver cirrhosis or cancer, etc.

BRIEF DESCRIPTION OF THE DRAWINGS

FIG. 3 shows BLT2 mRNA expression in mouse skin keratinocytes.

BEST MODE FOR CARRYING OUT THE INVENTION

Figure 1:
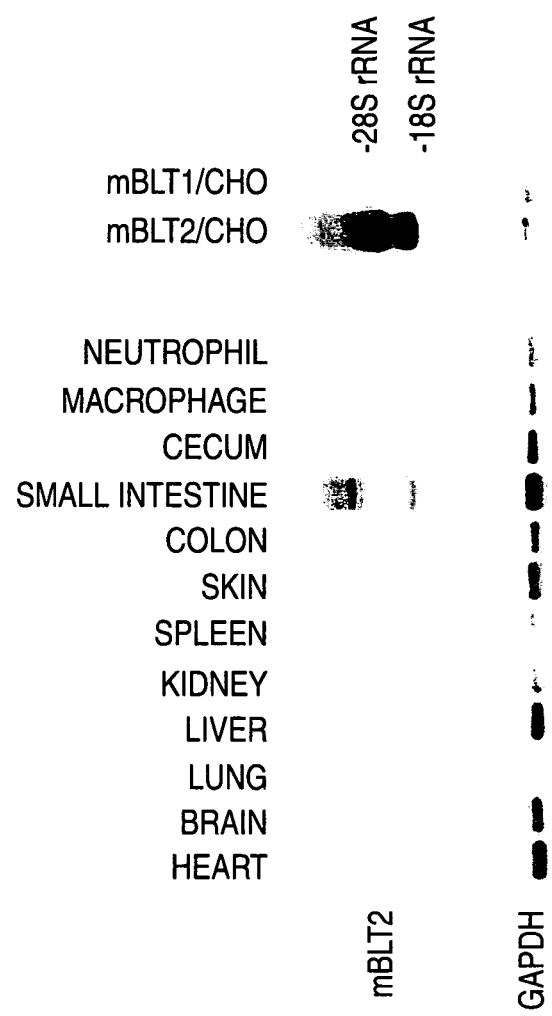
FIG. 1 shows BLT2 mRNA expression pattern in each mouse tissue (northern blotting).

Hereafter, examples illustrate the present invention but do not limit the present invention. The solvent in parentheses shown in chromatographic separation or TLC represents a used dissolution medium or eluent and the ratio of both solvents represents the volume ratio.

NMR data is the data of $^1$H-NMR unless otherwise stated.

The solvent in parentheses of NMR represents a solvent used for measurement unless otherwise stated, MS is carried out in ESI (electron spray ion) method, in which cation (pos.) was detected.

The condition of HPLC is as follows.
(1) Condition A (analysis)
Instrument: Waters LC/MS
Column: Xterra (registered trademark) MS C185 µm, 4.6×50 mm I.D
Flow rate: 3 mL/min
Solvent: A liquid: 0.1% trifluoroacetic acid solution
B liquid: trifluoroacetic acid-0.1% acetonitrile solution

TABLE 1

| Time (min) | A liquid | B liquid |
|---|---|---|
| 0 | 95 | 5 |
| 0.5 | 95 | 5 |
| 3 | 0 | 100 |
| 3.5 | 0 | 100 |
| 3.51 | 95 | 5 |
| 5 | 95 | 5 |

EXAMPLE 1(1) TO 1(75)

<Reaction 1>

Wang resin (Argonaut Technology) was washed with N,N-dimethylformamide. Three equivalents of iodobenzoic acid, 1-ethyl-3-[3-(dimethylamino)propyl]carbodiimide and 1-hydroxybenzotriazole, which correspond to N,N-dimethylformamide suspension for Wang resin, were added to Wang resin respectively and diisopropylethylamine (5 equivalents) was added. The reaction mixture was reacted during 18 hours at room temperature. The resin was filtered and sequentially washed with N,N-dimethylformamide, tetrahydrofuran, methanol and 1,2-dimethoxyethane.

<Reaction 2>

The corresponding formylphenyl borane acid (2 equivalents) and 2 mol/L potassium carbonate solution (2 equivalents) were added to the obtained resin suspension in degassed 1,2-dimethoxyethane. The catalyst quantity of bis(triphenylphosphine)palladium dichloride was added there. The reaction mixture was reacted for 16 hours at 60° C. and then cooled up to room temperature and filtered. The resin was washed with 1,2-dimethoxyethane/water (2:1), 1,2-dimethoxyethane, N,N-dimethylformamide, tetrahydrofuran and methanol.

<Reaction 3>

The obtained resin was washed with 1% acetate/1,2-dichloroethane. Further, the corresponding 0.5 mol/L amine compound (5 equivalents) in 1% acetate/1,2-dichloroethane solution was added and reacted for 5 hours at room temperature. 0.5 mol/L tetrabutylammonium borohydride in 1% acetate/1,2-dichloroethane solution (5 equivalents) was added to the above mixture and then reacted overnight. The resin was filtered and washed with methanol, tetrahydrofuran and N,N-dimethylformamide.

<Reaction 4>

The obtained resin was washed with 1,2-dichloroethane. Further, the corresponding 1 mol/L acylchloride in 1,2-dichloroethane solution (5 equivalents) and diisopropylethylamine in 1,2-dichloroethane solution (7.5 equivalents) were sequentially added. The reaction mixture was reacted overnight, and the resin was filtered and washed with 1,2-dichloroethane, methanol and tetrahydrofuran.

<Reaction 5>

Methanol/30% tetrahydrofuran in 0.1 mol/L sodium methylate (1 equivalent) solution was added to the obtained resin. 0.5 mol/L sodium hydroxide solution (1 equivalent) was added to the mixture to be concentrated. The following compound of the present invention was obtained.

EXAMPLE 1(1)

sodium 2'-{[benzyl(phenylacetyl)amino]methyl}1,1'-biphenyl-2-carboxylate

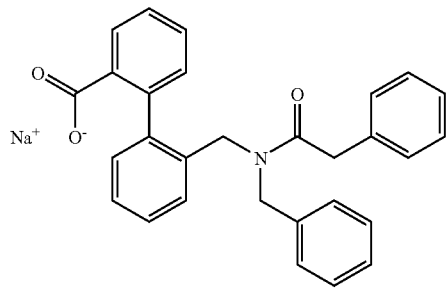 [SMILES: [Na+] ; O=C([O-])c1ccccc1-c1ccccc1CN(Cc1ccccc1)C(=O)Cc1ccccc1]

HPLC retention time: 4.03 minutes; MS: 300.25, 436.34 (M+H)+.

EXAMPLE 1(2)

sodium 2'-{[(phenylacetyl)(3-phenylpropyl)amino]methyl}-1,1'-biphenyl-2-carboxylate HPLC retention time: 4.14 minutes; MS: 328, 464 (M+H)+.

EXAMPLE 1(3)

sodium 2'-{[phenyl(3-phenylpropanoyl)amino]methyl}-1,1'-biphenyl-2-carboxylate

HPLC retention time: 4.12 minutes; MS: 286, 436 (M+H)+.

EXAMPLE 1(4)

sodium 2'-{[(2-phenylethyl)(3-phenylpropanoyl)amino]methyl}-1,1'-biphenyl-2-carboxylate HPLC retention time: 4.16 minutes; MS: 464 (M+H)+.

EXAMPLE 1(5)

sodium 2'-{[(3-phenylpropanoyl)(3-phenylpropyl)amino]methyl}-1,1'-biphenyl-2-carboxylate HPLC retention time: 4.23 minutes; MS: 478 (M+H)+.

EXAMPLE 1(6)

sodium 2'-{[(3-phenylpropanoyl)(1-propylbutyl)amino]methyl}-1,1'-biphenyl-2-carboxylate HPLC retention time: 4.37 minutes; MS: 458 (M+H)+.

EXAMPLE 1(7)

sodium 2'-{[(4-chlorobenzoyl)(phenyl)amino]methyl}-1,1'-biphenyl-2-carboxylate

HPLC retention time: 4.1 minutes; MS: 232, 442 (M+H)+.

EXAMPLE 1(8)

sodium 2'-{[(4-chlorobenzoyl)(3-phenylpropyl)amino])}-1,1'-biphenyl-2-carboxylate HPLC retention time: 4.23 minutes; MS: 328, 484 (M+H)+.

EXAMPLE 1(9)

sodium 2'-{[(4-chlorobenzoyl)(1-propylbutyl)amino]methyl}-1,1'-biphenyl-2-carboxylate HPLC retention time: 4.41 minutes; MS: 464 (M+H)+.

EXAMPLE 1(10)

sodium 2'-{[(4-methoxybenzoyl)(3-phenylpropyl)amino]methyl}-1,1'-biphenyl-2-carboxylate HPLC retention time: 4.09 minutes; MS: 480 (M+H)+.

EXAMPLE 1(11)

sodium 3'-{[phenyl(phenylacetyl)amino]methyl}-1,1'-biphenyl-2-carboxylate

HPLC retention time: 4.02 minutes; MS: 422 (M+H)+.

EXAMPLE 1(12)

sodium 3'-{[(phenylacetyl)(1-propylbutyl)amino]methyl}-1,1'-biphenyl-3-carboxylate HPLC retention time: 4.31 minutes; MS: 444 (M+H)+.

EXAMPLE 1(13)

sodium 3'-{[phenyl(3-phenylpropanoyl)amino]methyl}-1,1'-biphenyl-3-carboxylate

HPLC retention time: 4.12 minutes; MS: 436 (M+H)+.

EXAMPLE 1(14)

sodium 3'-{[benzyl(3-phenylpropanoyl)amino]methyl}-1,1'-biphenyl-3-carboxylate

HPLC retention time: 4.15 minutes; MS: 450 (M+H)+.

EXAMPLE 1(15)

sodium 3'-{[(2-phenylethyl)(3-phenylpropanoyl)amino]methyl}-1,1'-biphenyl-3-carboxylate HPLC retention time: 4.19 minutes; MS: 464 (M+H)+.

EXAMPLE 1(16)

sodium 3'-{[(3-phenylpropanoyl)(3-phenylpropyl)amino]methyl}-1,1'-biphenyl-3-carboxylate HPLC retention time: 4.24 minutes; MS: 478 (M+H)+.

EXAMPLE 1(17)

sodium 3'-{[butyl(3-phenylpropanoyl)amino]methyl}-1,1'-biphenyl-3-carboxylate

HPLC retention time: 4.14 minutes; MS: 416 (M+H)+.

EXAMPLE 1(18)

sodium 3'-{[(3-phenylpropanoyl)(1-propylbutyl)amino]methyl}-1,1'-biphenyl-3-carboxylate HPLC retention time: 4.4 minutes; MS: 458 (M+H)+.

EXAMPLE 1(19)

sodium 3'-{[(4-chlorobenzoyl)(phenyl)amino]methyl}-1,1'-biphenyl-3-carboxylate

HPLC retention time: 4.11 minutes; MS: 442 (M+H)+.

EXAMPLE 1(20)

sodium 3'-{[benzyl(4-chlorobenzoyl)amino]methyl}-1,1'-biphenyl-3-carboxylate

HPLC retention time: 4.19 minutes; MS: 456 (M+H)+.

EXAMPLE 1(21)

sodium 3'-{[(4-chlorobenzoyl)(2-phenylethyl)amino]methyl}-1,1'-biphenyl-3-carboxylate HPLC retention time: 4.23 minutes; MS: 470 (M+H)+.

EXAMPLE 1(22)

sodium 3'-{[(4-chlorobenzoyl)(1-propylbutyl)amino]methyl}-1,1'-biphenyl-3-carboxylate HPLC retention time: 4.43 minutes; MS: 464 (M+H)+.

EXAMPLE 1(23)

sodium 3'-{[(4-methoxybenzoyl)(phenyl)amino]methyl}-1,1'-biphenyl-3-carboxylate

HPLC retention time: 3.96 minutes; MS: 438 (M+H)+.

EXAMPLE 1(24)

sodium 3'-{[pentanoyl(3-phenylpropyl)amino]methyl}-1,1'-biphenyl-3-carboxylate

HPLC retention time: 4.21 minutes; MS: 430 (M+H)+.

EXAMPLE 1(25)

sodium 3'-{[benzyl(phenylacetyl)amino]methyl}-1,1'-biphenyl-4-carboxylate

HPLC retention time: 4.06 minutes; MS: 436 (M+H)+.

EXAMPLE 1(26)

sodium 3'-{[(phenylacetyl)(2-phenylethyl)amino]methyl)}-1,1'-biphenyl-4-carboxylate HPLC retention time: 4.1 minutes; MS: 450 (M+H)+.

EXAMPLE 1(27)

sodium 3'-{[(phenylacetyl)(3-phenylpropyl)amino]methyl}-1,1'-biphenyl-4-carboxylate HPLC retention time: 4.15 minutes; MS: 464 (M+H)+.

EXAMPLE 1(28)

sodium 3'-{[(phenylacetyl)(1-propylbutyl)amino]methyl}-1,1'-biphenyl-4-carboxylate HPLC retention time: 4.31 minutes; MS: 444 (M+H)+.

EXAMPLE 1(29)

sodium 3'-{[phenyl(3-phenylpropanoyl)amino]methyl}-1,1'-biphenyl-4-carboxylate

HPLC retention time: 4.1 minutes; MS: 436 (M+H)+.

EXAMPLE 1(30)

sodium 3'-{[benzyl(3-phenylpropanoyl)amino]methyl}-1,1'-biphenyl-4-carboxylate

HPLC retention time: 4.14 minutes; MS: 450 (M+H)+.

EXAMPLE 1(31)

sodium 3'-{[(2-phenylethyl)(3-phenylpropanoyl)amino]methyl}-1,1'-biphenyl-4-carboxylate HPLC retention time: 4.18 minutes; MS: 464 (M+H)+.

EXAMPLE 1(32)

sodium 3'-{[(3-phenylpropanoyl)(3-phenylpropyl)amino]methyl}-1,1'-biphenyl-4-carboxylate HPLC retention time: 4.23 minutes; MS: 478 (M+H)+.

EXAMPLE 1(33)

sodium 3'-{[benzyl(4-chlorobenzoyl)amino]methyl}-1,1'-biphenyl-4-carboxylate

HPLC retention time: 4.17 minutes; MS: 456 (M+H)+.

EXAMPLE 1(34)

sodium 3'-{[(4-chlorobenzoyl)(2-phenylethyl)amino]methyl}-1,1'-biphenyl-4-carboxylate HPLC retention time: 4.2 minutes; MS: 470 (M+H)+.

EXAMPLE 1(35)

sodium 3'-{[(4-chlorobenzoyl)(3-phenylpropyl)amino]methyl}-1,1'-biphenyl-4-carboxylate HPLC retention time: 4.25 minutes; MS: 484 (M+H)+.

EXAMPLE 1(36)

sodium 3'-{[benzyl(4-methoxybenzoyl)amino]methyl} 1,1'-biphenyl-4-carboxylate

HPLC retention time: 4.04 minutes; MS: 452 (M+H)+.

EXAMPLE 1(37)

sodium 3'-{[(4-methoxybenzoyl)(3-phenylpropyl)amino]methyl}-1,1'-biphenyl-4-carboxylate HPLC retention time: 4.11 minutes; MS: 480 (M+H)+.

EXAMPLE 1(38)

sodium 3'-{[benzyl(cyclopentylcarbonyl)amino]methyl}-1,1'-biphenyl-4-carboxylate HPLC retention time: 4.13 minutes; MS: 414 (M+H)+.

EXAMPLE 1(39)

sodium 3'-{[(cyclopentylcarbonyl)(3-phenylpropyl)amino]methyl}-1,1'-biphenyl-4-carboxylate HPLC retention time: 4.24 minutes; MS: 442 (M+H)+.

EXAMPLE 1(40)

sodium 3'-{[pentanoyl(3-phenylpropyl)amino]methyl}-1,1'-biphenyl-4-carboxylate

HPLC retention time: 4.19 minutes; MS: 430 (M+H)+.

EXAMPLE 1(41)

sodium 4'-{[benzoyl(3-phenylpropyl)amino]methyl}-1,1'-biphenyl-4-carboxylate

HPLC retention time: 4.11 minutes; MS: 450 (M+H)+.

EXAMPLE 1(42)

sodium 4'-{[benzyl(phenylacetyl)amino]methyl}-1,1'-biphenyl-4-carboxylate

HPLC retention time: 4.06 minutes; MS: 436 (M+H)+.

EXAMPLE 1(43)

sodium 4'-{[(phenylacetyl)(2-phenylethyl)amino]methyl}-1,1'-biphenyl-4-carboxylate HPLC retention time: 4.09 minutes; MS: 450 (M+H)+.

EXAMPLE 1(44)

sodium 4'-{[(phenylacetyl)(3-phenylpropyl)amino]methyl}-1,1'-biphenyl-4-carboxylate HPLC retention time: 4.16 minutes; MS: 464 (M+H)+.

EXAMPLE 1(45)

sodium 4'-{[butyl(phenylacetyl)amino]methyl}-1,1'-biphenyl-4-carboxylate

HPLC retention time: 4.04 minutes; MS: 402 (M+H)+.

EXAMPLE 1(46)

sodium 4'-{[(phenylacetyl)(1-propylbutyl)amino]methyl}-1,1'-biphenyl-4-carboxylate HPLC retention time: 4.34 minutes; MS: 444 (M+H)+.

EXAMPLE 1(47)

sodium 4'-{[(2-phenylethyl)(3-phenylpropanoyl)amino]methyl}-1,1'-biphenyl-4-carboxylate HPLC retention time: 4.17 minutes; MS: 464 (M+H)+.

EXAMPLE 1(48)

sodium 4'-{[(3-phenylpropanoyl)(3-phenylpropyl)amino]methyl}-1,1'-biphenyl-4-carboxylate HPLC retention time: 4.23 minutes; MS: 478 (M+H)+.

EXAMPLE 1(49)

sodium 4'-{[butyl(3-phenylpropanoyl)amino]methyl}-1,1'-biphenyl-4-carboxylate

HPLC retention time: 4.14 minutes; MS: 416 (M+H)+.

EXAMPLE 1(50)

sodium 4'-{[(3-phenylpropanoyl)(1-propylbutyl)amino]methyl}-1,1'-biphenyl-4-carboxylate HPLC retention time: 4.42 minutes; MS: 458 (M+H)+.

EXAMPLE 1(51)

sodium 4'-{[(4-chlorobenzoyl)(phenyl)amino]methyl}-1,1'-biphenyl-4-carboxylate

HPLC retention time: 4.09 minutes; MS: 442 (M+H)+.

EXAMPLE 1(52)

sodium 4'-{[(4-chlorobenzoyl)(2-phenylethyl)amino]methyl}-1,1'-biphenyl-4-carboxylate HPLC retention time: 4.18 minutes; MS: 470 (M+H)+.

EXAMPLE 1(53)

sodium 4'-{[(4-chlorobenzoyl)(3-phenylpropyl)amino]methyl}-1,1'-biphenyl-4-carboxylate HPLC retention time: 4.24 minutes; MS: 485 (M+H)+.

EXAMPLE 1(54)

sodium 4'-{[butyl(4-chlorobenzoyl)amino]methyl}-1,1'-biphenyl-4-carboxylate

HPLC retention time: 4.17 minutes; MS: 422 (M+H)+.

EXAMPLE 1(55)

sodium 4'-{[(4-methoxybenzoyl)(3-phenylpropyl)amino]methyl} 1,1'-biphenyl-4-carboxylate HPLC retention time: 4.09 minutes; MS: 480 (M+H)+.

EXAMPLE 1(56)

sodium 4'-{[(cyclopentylcarbonyl)(2-phenylethyl)amino]methyl}-1,1'-biphenyl-4-carboxylate HPLC retention time: 4.17 minutes; MS: 428 (M+H)+.

EXAMPLE 1(57)

sodium 4'-{[(cyclopentylcarbonyl)(3-phenylpropyl)amino]methyl}-1,1'-biphenyl-4-carboxylate HPLC retention time: 4.25 minutes; MS: 442 (M+H)+.

EXAMPLE 1(58)

sodium 4'-{[(cyclopentylcarbonyl)(1-propylbutyl)amino]methyl}-1,1'-biphenyl-4-carboxylate HPLC retention time: 4.43 minutes; MS: 422 (M+H)+.

EXAMPLE 1(59)

sodium 4'-{[pentanoyl(3-phenylpropyl)amino]methyl}-1,1'-biphenyl-4-carboxylate

HPLC retention time: 4.19 minutes; MS: 430 (M+H)+.

EXAMPLE 1(60)

sodium 3'-{[(4-methoxybenzoyl)(4-phenylbutyl)amino]methyl} 1,1'-biphenyl-3-carboxylate HPLC retention time: 4.15 minutes; MS: 494 (M+H)+.

EXAMPLE 1(61)

sodium 4'-{[(4-methoxybenzoyl)(3-phenylpropyl)amino]methyl}-1,1'-biphenyl-4-carboxylate HPLC retention time: 4.02 minutes; MS: 480 (M+H)+.

EXAMPLE 1(62)

sodium 4'-{[(4-methoxybenzoyl)(4-phenylbutyl)amino]methyl}-1,1'-biphenyl-4-carboxylate HPLC retention time: 4.11 minutes; MS: 494 (M+H)+.

EXAMPLE 1(63)

sodium 4'-{[(2,2-diphenylethyl)(4-methoxybenzoyl)amino]methyl}-1,1'-biphenyl-4-carboxylate HPLC retention time: 4.15 minutes; MS: 542 (M+H)+.

EXAMPLE 1(64)

sodium 4'-{[(2-cyclohexa-1-en-1-ylethyl)(4-methoxybenzoyl)amino]methyl}-1,1'-biphenyl-4-carboxylate HPLC retention time: 4.19 minutes; MS: 470 (M+H)+.

EXAMPLE 1(65)

sodium 4'-{[{[(1S,2R,5S)-6,6-dimethylbicyclo[3.1.1]hepta-2-yl]methyl}(4-methoxybenzoyl)amino]methyl}-1,1'-biphenyl-4-carboxylate HPLC retention time: 4.35 minutes; MS: 498 (M+H)+.

EXAMPLE 1(66)

sodium 4'-{[(2-ethylhexyl)(4-methoxybenzoyl)amino]methyl}-1,1'-biphenyl-4-carboxylate HPLC retention time: 4.33 minutes; MS: 474 (M+H)+.

EXAMPLE 1(67)

sodium 4'-{[[2-(4-chlorophenyl)ethyl](pentanoyl)amino]methyl}-1,1'-biphenyl-4-carboxylate HPLC retention time: 4.19 minutes; MS: 450 (M+H)+.

EXAMPLE 1(68)

sodium 4'-{[[2-(2-chlorophenyl)ethyl](pentanoyl)amino]methyl}-1,1'-biphenyl-4-carboxylate HPLC retention time: 4.21 minutes; MS: 450 (M+H)+.

EXAMPLE 1(69)

sodium 4'-{[[2-(2-methoxyphenyl)ethyl](pentanoyl)amino]methyl}-1,1'-biphenyl-4-carboxylate HPLC retention time: 4.10 minutes; MS: 446 (M+H)+.

EXAMPLE 1(70)

sodium 4'-{[(2,2-diphenylethyl)(pentanoyl)amino]methyl}-1,1'-biphenyl-4-carboxylate HPLC retention time: 4.26 minutes; MS: 492 (M+H)+.

EXAMPLE 1(71)

sodium 4'-{[{[(1S,2R,5S)-6,6-dimethylbicyclo[3.1.1]hepta-2-yl]methyl}(pentanoyl)amino]methyl}-1,1'-biphenyl-4-carboxylate HPLC retention time: 4.52 minutes; MS: 448 (M+H)+.

EXAMPLE 1(72)

sodium 4'-{[(cyclopentylcarbonyl)(2-phenylethyl)amino]methyl}-1,1'-biphenyl-4-carboxylate HPLC retention time: 4.11 minutes; MS: 428 (M+H)+.

EXAMPLE 1(73)

sodium 4'-{[(cyclopentylcarbonyl)(3-phenylpropyl)amino]methyl}-1,1'-biphenyl-4-carboxylate HPLC retention time: 4.17 minutes; MS: 442 (M+H)+.

EXAMPLE 1(74)

sodium 4'-{[(cyclopentylcarbonyl)(2,2-diphenylethyl)amino]methyl}-1,1'-biphenyl-4-carboxylate HPLC retention time: 4.28 minutes; MS: 504 (M+H)+.

EXAMPLE 1(75)

sodium 4'-[((cyclopentylcarbonyl){[(1S,2R5S)-6,6-dimethylbicyclo[3.1.1]hepta-2-yl]methyl}amino)methyl]-1,1'-biphenyl-4-carboxylate HPLC retention time: 4.59 minutes; MS: 460 (M+H)+.

EXAMPLE 2(1) to 2(43)

The resin obtained in Reaction 3 on Example 1 was washed with 1% acetate/N,N-dimethylformamide solution. Further, the corresponding 1% acetate/N,N-dimethylformamide solution in 0.5 mol/L aldehyde derivative (5 equivalents) was added and reacted for 5 hours at room temperature. N,N-dimethylformamide solution in 0.5 mol/L sodium triacetoxyborohydride (5 equivalents) was added to the mixture and then reacted overnight. The resin was filtered and washed with methanol, N,N-dimethylformamide, tetrahydrofuran and 1,2-dichloroethane. Trifluoroacetic acid/20% 1,2-dichloroethane was added to the obtained resin and reacted for 30 minutes. The solution obtained by filtering the mixture was concentrated to obtain the following compound of the present invention.

EXAMPLE 2(1)

3'-{[benzyl(4-chlorobenzyl)amino]methyl} 1,1'-biphenyl-2-carboxylic acid trifluoroacetate

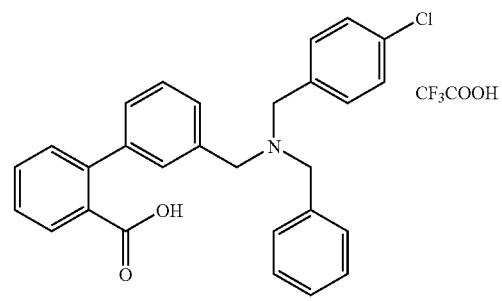

HPLC retention time: 3.6 minutes; MS: 442 (M+H)+.

EXAMPLE 2(2)

4'-{[(4-cyanobenzyl)(1-propylbutyl)amino]methyl}-1,1'-biphenyl-2-carboxylic acid trifluoroacetate HPLC retention time: 3.59 minutes; MS: 441 (M+H)+.

EXAMPLE 2(3)

2'-[(dibenzylamino)methyl]-1,1'-biphenyl-3-carboxylic acid trifluoroacetate

HPLC retention time: 3.47 minutes; MS: 408 (M+H)+.

EXAMPLE 2(4)

2'-{[(4-chlorobenzyl)(3-phenylpropyl)amino]methyl}-1,1'-biphenyl-3-carboxylic acid trifluoroacetate HPLC retention time: 3.64 minutes; MS: 470 (M+H)+.

EXAMPLE 2(5)

2'-{[benzyl(3-phenylpropyl)amino]methyl} 1,1'-biphenyl-3-carboxylic acid trifluoroacetate HPLC retention time: 3.56 minutes; MS: 436 (M+H)+.

EXAMPLE 2(6)

2'-{[(2-phenylethyl)(3-phenylpropyl)amino]methyl}-1,1'-biphenyl-3-carboxylic acid trifluoroacetate HPLC retention time: 3.62 minutes; MS: 450 (M+H)+.

EXAMPLE 2(7)

3'-{[(4-cyanobenzyl)(3-phenylpropyl)amino]methyl} 1,1'-biphenyl-3-carboxylic acid trifluoroacetate HPLC retention time: 3.55 minutes; MS: 461 (M+H)+.

EXAMPLE 2(8)

3'-{[benzyl(3-phenylpropyl)amino]methyl}-1,1'-biphenyl-3-carboxylic acid trifluoroacetate HPLC retention time: 3.63 minutes; MS: 436 (M+H)+.

EXAMPLE 2(9)

3'-{[bis(3-phenylpropyl)amino]methyl}-1,1'-biphenyl-3-carboxylic acid trifluoroacetate HPLC retention time: 3.72 minutes; MS: 464 (M+H)+.

EXAMPLE 2(10)

4'-{[(4-methoxybenzyl)(2-phenylethyl)amino]methyl}-1,1'-biphenyl-3-carboxylic acid trifluoroacetate HPLC retention time: 3.58 minutes; MS: 452 (M+H)+.

EXAMPLE 2(11)

2'-{[benzyl(3-phenylpropyl)amino]methyl}-1,1'-biphenyl-4-carboxylic acid trifluoroacetate HPLC retention time: 3.51 minutes; MS: 436 (M+H)+.

EXAMPLE 2(12)

2'-{[(4-chlorobenzyl)(3-phenylpropyl)amino]methyl}-1,1'-biphenyl-4-carboxylic acid trifluoroacetate HPLC retention time: 3.59 minutes; MS: 470 (M+H)+.

EXAMPLE 2(13)

2'-{[butyl(4-chlorobenzyl)amino]methyl}-1,1'-biphenyl-4-carboxylic acid trifluoroacetate HPLC retention time: 3.46 minutes; MS: 408 (M+H)+.

EXAMPLE 2(14)

2'-{[benzyl(4-cyanobenzyl)amino]methyl}-1,1'-biphenyl-4-carboxylic acid trifluoroacetate HPLC retention time: 3.55 minutes; MS: 433 (M+H)+.

EXAMPLE 2(15)

2'-{[(4-cyanobenzyl)(3-phenylpropyl)amino]methyl} 1,1'-biphenyl-4-carboxylic acid trifluoroacetate HPLC retention time: 3.48 minutes; MS: 461 (M+H)+.

EXAMPLE 2(16)

2'-{[bis(3-phenylpropyl)amino]methyl}-1,1'-biphenyl-4-carboxylic acid trifluoroacetate HPLC retention time: 3.61 minutes; MS: 464 (M+H)+.

EXAMPLE 2(17)

2'-{[benzyl(cyclohexylmethyl)amino]methyl}-1,1'-biphenyl-4-carboxylic acid trifluoroacetate HPLC retention time: 3.51 minutes; MS: 414 (M+H)+.

EXAMPLE 2(18)

3'-{[benzyl(3-phenylpropyl)amino]methyl}-1,1'-biphenyl-4-carboxylic acid trifluoroacetate HPLC retention time: 3.57 minutes; MS: 436 (M+H)+.

EXAMPLE 2(19)

3'-{[(4-cyanobenzyl)(2-phenylethyl)amino]methyl}-1,1'-biphenyl-4-carboxylic acid trifluoroacetate HPLC retention time: 3.47 minutes; MS: 447 (M+H)+.

EXAMPLE 2(20)

3'-{[(cyclohexylmethyl)(2-phenylethyl)amino]methyl}-1,1'-biphenyl-4-carboxylic acid trifluoroacetate HPLC retention time: 3.64 minutes; MS: 428 (M+H)+.

EXAMPLE 2(21)

4'-[(dibenzylamino)methyl]-1,1'-biphenyl-4-carboxylic acid trifluoroacetate

HPLC retention time: 3.46 minutes; MS: 408 (M+H)+.

EXAMPLE 2(22)

4'-{([benzyl(2-phenylethyl)amino]methyl}-1,1'-biphenyl-4-carboxylic acid trifluoroacetate HPLC retention time: 3.51 minutes; MS: 422 (M+H)+.

EXAMPLE 2(23)

4'-{[benzyl(3-phenylpropyl)amino]methyl}-1,1'-biphenyl-4-carboxylic acid trifluoroacetate HPLC retention time: 3.56 minutes; MS: 436 (M+H)+.

EXAMPLE 2(24)

4'-{[benzyl(butyl)amino]methyl}-1,1'-biphenyl-4-carboxylic acid trifluoroacetate HPLC retention time: 3.4 minutes; MS: 374 (M+H)+.

EXAMPLE 2(25)

4'-{[(4-chlorobenzyl)(2-phenylethyl)amino]methyl}-1,1'-biphenyl-4-carboxylic acid trifluoroacetate HPLC retention time: 3.61 minutes; MS: 456 (M+H)+.

EXAMPLE 2(26)

4'-{[(4-chlorobenzyl)(3-phenylpropyl)amino]methyl}-1,1'-biphenyl-4-carboxylic acid trifluoroacetate HPLC retention time: 3.66 minutes; MS: 470 (M+H)+.

EXAMPLE 2(27)

4'-{[(4-chlorobenzyl)(2-methoxyethyl)amino]methyl}-1,1'-biphenyl-4-carboxylic acid trifluoroacetate HPLC retention time: 3.39 minutes; MS: 410 (M+H)+.

EXAMPLE 2(28)

4'-{[butyl(4-chlorobenzyl)amino]methyl}-1,1'-biphenyl-4-carboxylic acid trifluoroacetate HPLC retention time: 3.51 minutes; MS: 408 (M+H)+.

EXAMPLE 2(29)

4'-{[(4-methoxybenzyl)(2-phenylethyl)amino]methyl}-1,1'-biphenyl-4-carboxylic acid trifluoroacetate HPLC retention time: 3.52 minutes; MS: 452 (M+H)+.

EXAMPLE 2(30)

4'-{[(4-methoxybenzyl)(3-phenylpropyl)amino]methyl} 1,1'-biphenyl-4-carboxylic acid trifluoroacetate HPLC retention time: 3.58 minutes; MS: 466 (M+H)+.

EXAMPLE 2(31)

4'-{[(4-cyanobenzyl)(2-phenylethyl)amino]methyl}-1,1'-biphenyl-4-carboxylic acid trifluoroacetate HPLC retention time: 3.46 minutes; MS: 447 (M+H)+.

EXAMPLE 2(32)

4'-{[(4-cyanobenzyl)(3-phenylpropyl)amino]methyl}-1,1'-biphenyl-4-carboxylic acid trifluoroacetate HPLC retention time: 3.53 minutes; MS: 461 (M+H)+.

EXAMPLE 2(33)

4'-{[butyl(4-cyanobenzyl)amino]methyl} 1,1'-biphenyl-4-carboxylic acid trifluoroacetate HPLC retention time: 3.35 minutes; MS: 399 (M+H)+.

EXAMPLE 2(34)

4'-{[benzyl(3-phenylpropyl)amino]methyl}-1,1'-biphenyl-4-carboxylic acid trifluoroacetate HPLC retention time: 3.55 minutes; MS: 435 (M+H)+.

EXAMPLE 2(35)

4'-{[(2-phenylethyl)(3-phenylpropyl)amino]methyl}-1,1'-biphenyl-4-carboxylic acid trifluoroacetate HPLC retention time: 3.64 minutes; MS: 450 (M+H)+.

EXAMPLE 2(36)

4'-{[bis(3-phenylpropyl)amino]methyl}-1,1'-biphenyl-4-carboxylic acid trifluoroacetate HPLC retention time: 3.69 minutes; MS: 464 (M+H)+.

EXAMPLE 2(37)

4'-{[(3-phenylpropyl)(1-propylbutyl)amino]methyl}-1,1'-biphenyl-4-carboxylic acid trifluoroacetate HPLC retention time: 3.75 minutes; MS: 444 (M+H)+.

EXAMPLE 2(38)

4'-{[benzyl(cyclohexylmethyl)amino]methyl}-1,1'-biphenyl-4-carboxylic acid trifluoroacetate HPLC retention time: 3.57 minutes; MS: 414 (M+H)+.

EXAMPLE 2(39)

4'-{[(cyclohexylmethyl)(2-phenylethyl)amino]methyl} 1,1'-biphenyl-4-carboxylic acid trifluoroacetate HPLC retention time: 3.63 minutes; MS: 428 (M+H)+.

EXAMPLE 2(40)

4'-{[butyl(cyclohexylmethyl)amino]methyl}-1,1'-biphenyl-4-carboxylic acid trifluoroacetate HPLC retention time: 3.52 minutes; MS: 380 (M+H)+.

EXAMPLE 2(41)

4'-{[benzyl(pentyl)amino]methyl}-1,1'-biphenyl-4-carboxylic acid trifluoroacetate HPLC retention time: 3.49 minutes; MS: 388 (M+H)+.

EXAMPLE 2(42)

4'-{[pentyl(2-phenylethyl)amino]methyl}-1,1'-biphenyl-4-carboxylic acid trifluoroacetate HPLC retention time: 3.59 minutes; MS: 402 (M+H)+.

EXAMPLE 2(43)

4'-{[(3-phenylpropyl)(pyridin-2-ylmethyl)amino]methyl}-1,1'-biphenyl-4-carboxylic acid trifluoroacetate HPLC retention time: 3.46 minutes; MS: 437 (M+H)+.

EXAMPLE 3 methyl 4'-(bromomethyl)biphenyl-2-carboxylate 2,2-azobisisobutyronitrile (6.91 g) and N-bromosuccinimide (302 mg) were added to methyl 4'-methlbiphenyl-2-carboxylate (8.78 g) in carbon tetrachloride (500 mL) solution. The mixture was refluxed for 6 hours under argon gas and filtered after being cooled to room temperature, and then concentrated. The titled compound (9.30 g) having the following physical data was obtained by purifying the obtained residue by silica gel column chromatography (ethyl acetate:hexane=1:5).

TLC: Rf 0.59 (ethyl acetate:hexane=1:4);
NMR (CDCl$_3$): δ 7.89-7.82 (m, 1H), 7.63-7.26 (m, 7H), 4.55 (s, 2H), 3.65 (s, 2H).

EXAMPLE 4 methyl 4'-formylbiphenyl-2-carboxylate 2-nitropropane (3.56 g) was added to a solution that sodium (85 mg) was added to ethanol (50 mL) little by little. Further, the compound (8.40 g) prepared in Example 3 in ethanol solution (10 mL) was added and stirred for 4 hours at 70° C. The reaction mixture was concentrated and extracted with ethyl acetate after adding water. The extract was sequentially washed with 1 mol/L sodium hydroxide solution and saturated brine and dried by anhydrous sodium sulfate, and then concentrated. The titled compound (5.02 g) having the following physical data was obtained by purifying the obtained residue by silica gel column chromatography (ethyl acetate:hexane=1:5).

TLC: Rf 0.50 (ethyl acetate:hexane=1:2);
NMR (CDCl$_3$): δ 10.07 (s, 1H), 7.96-7.89 (m, 3H), 7.63-7.34 (m, 5H), 3.66 (s, 3H).

EXAMPLE 5 methyl 4'-[(benzylamino)methyl]biphenyl-2-carboxylate

Benzylamine (128 mg) was added to the compound (120 mg) prepared in Example 4 in methanol solution (3 mL) and stirred for 4 hours at room temperature. Cyano sodium borohydride (62 mg) was added to the reaction mixture and then acetic acid was dropped until pH.5.5 and stirred for 1 hour at room temperature. The reaction mixture was concentrated and alkalinized with 5 mol/L sodium hydroxide solution, and then extracted with ethyl acetate. The organic layer was washed with saturated brine and dried by anhydrous sodium sulfate, and then concentrated. The titled compound (94 mg) having the following physical data was obtained by purifying the obtained residue by silica gel column chromatography (chloroform:hexane=30:1).

TLC: Rf 0.51 (chloroform:methanol=9:1);
NMR (CDCl$_3$): δ 7.85-7.79 (m, 1H), 7.58-7.22 (m, 12H), 3.87 (s, 2H), 3.86 (s, 2H), 3.65 (s, 3H).

EXAMPLE 6 methyl 4'-{[benzyl(pentanoyl)amino]methyl}biphenyl-2-carboxylate

Pentanoyl chloride (62 μL) was added to the compound (85 mg) prepared in Example 5 in pyridine solution (2 mL) and stirred for 1.5 hours at room temperature. Further, water was added to the reaction mixture and extracted with ethyl acetate. The extract was sequentially washed with 1 mol/L hydrochloric acid, saturated sodium hydrogencarbonate solution and saturated brine and dried by anhydrous sodium sulfate, and then concentrated. The titled compound (101 mg) having the following physical data was obtained by purifying the obtained residue by silica gel column chromatography (ethyl acetate:hexane=1:2).

TLC: Rf 0.55 (ethyl acetate:hexane=1:2);
NMR (CDCl$_3$): δ 7.89-7.80 (m, 1H), 7.60-7.16 (m, 12H), 4.65 (s, 2H), 4.50 (s, 2H), 3.68 and 3.66 (s, 3H), 2.50-2.40 (m, 2H), 1.80-1.64 (m, 2H), 1.48-1.26 (m, 2H), 0.96-0.87 (m, 3H).

EXAMPLE 7

4'-{[benzyl(pentanoyl)amino]methyl}-1,1'-biphenyl-2-carboxylic acid

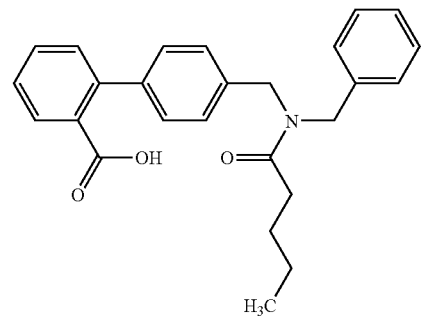 [SMILES: CCCCC(=O)N(Cc1ccccc1)Cc1ccc(-c2ccccc2C(=O)O)cc1]

5 mol/L sodium hydroxide solution (0.3 mL) was added to the compound (45 mg) prepared in Example 6 in a mixed solution of dioxane (2 mL) and methanol (1 mL) and stirred for 2 hours at 80° C. To acidify, 1 mol/L hydrochloric acid was added to the concentrated reaction mixture to be extracted with ethyl acetate. The organic layer was washed with saturated sodium and dried by anhydrous sodium sulfate, and then concentrated to obtain the titled compound (37 mg) having the following physical data.

TLC: Rf 0.59 (chloroform:methanol=9:1);
NMR (CDCl$_3$): δ 7.98-7.91 (m, 1H), 7.61-7.52 (m, 1H), 7.47-7.14 (m, 11H), 4.62 (s, 2H), 4.48 and 4.49 (s, 2H), 2.47-2.40 (m, 2H), 1.75-1.64 (m, 2H), 1.43-1.28 (m, 2H), 0.90 (t, J=7.2 Hz, 3H).

EXAMPLE 8 methyl 4'-(anilinomethyl)biphenyl-2-carboxylate

Phenylamine (56 mg) was added to the compound (120 mg) prepared in Example 4 in methanol solution (3 mL) and stirred for 4 hours at room temperature. The reaction mixture was added to sodium borohydride (37 mg) and stirred for 1.5 hours. To alkalinize, 5 mol/L sodium hydroxide solution was added to the concentrated reaction mixture and then extracted with ethyl acetate. The organic layer was washed with saturated sodium and dried by anhydrous sodium sulfate, and then concentrated to obtain the titled compound (124 mg) having the following physical data by purifying the obtained residue by silica gel column chromatography (diethyl ether:hexane=1:2).

TLC: Rf 0.42 (ethyl acetate:hexane=1:4);

NMR (CDCl3): δ 7.86-7.80 (m, 1H), 7.58-7.14 (m, 9H), 6.78-6.64 (m, 3H), 4.38 (s, 2H), 4.20-4.00 (br, 1H), 3.65 (s, 3H).

EXAMPLE 9

4'-{[pentanoyl(phenyl)amino]methyl}-1,1'-biphenyl-2-carboxylic acid

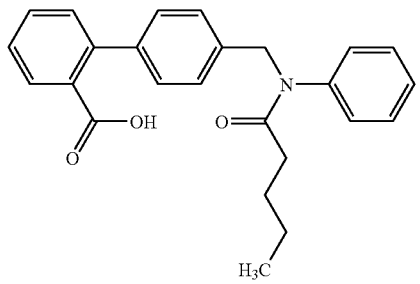 [SMILES: CCCCC(=O)N(Cc1ccc(-c2ccccc2C(=O)O)cc1)c1ccccc1]

The titled compound having the following physical data was obtained by the same procedures as a series of Example 6 and Example 7 using the compound prepared in Example 8.

TLC: Rf 0.59 (chloroform:methanol=9:1);

NMR (CDCl3): δ 7.92 (dd, J=7.6, 1.2 Hz, 1H), 7.60-7.51 (m, 1H), 7.46-7.16 (m, 9H), 7.00-6.93 (m, 2H), 4.90 (s, 2H), 2.06 (t, J=7.6 Hz, 2H), 1.65-1.49 (m, 2H), 1.30-1.10 (m, 2H), 0.79 (t, J=7.3 Hz, 3H).

EXAMPLE 10 methyl 4'-(hydroxymethyl)biphenyl-2-carboxylate

Sodium borohydride (111 mg) was added to the compound (400 mg) prepared in Example 4 in methanol solution (10 mL) and stirred for 1 hour at room temperature. The reaction mixture was concentrated and extracted with 1 mol/L hydrochloric acid and ethyl acetate. The organic layer was washed with saturated sodium and dried by anhydrous sodium sulfate, and then concentrated to obtain the titled compound (400 mg) having the following physical data.

TLC: Rf 0.33 (ethyl acetate:hexane=1:1);

NMR (CDCl3): δ 7.86-7.80 (m, 1H), 7.60-7.26 (m, 7H), 4.75 (s, 2H), 3.67 (s, 3H).

EXAMPLE 11 methyl 4'-(azidomethyl)biphenyl-2-carboxylate

Sodium azide (650 mg), triphenylphosphine (935 mg) and carbon tetrabromide (1.18 g) was added to the compound (345 mg) prepared in Example 10 in N,N-dimethylformamide (15 mL) solution and stirred for 2 hours at room temperature. Water was added to the reaction mixture, which was extracted with ethyl acetate. It was washed with saturated sodium and dried by anhydrous sodium sulfate, and then concentrated to the titled compound (380 mg) having the following physical data by purifying the obtained residue by silica gel column chromatography (ethyl acetate:hexane=1:6).

TLC: Rf 0.53 (ethyl acetate:hexane=1:4);

NMR (CDCl3): δ 7.86 (dd, J=7.7, 1.5 Hz, 1H), 7.60-7.30 (m, 7H), 4.40 (s, 2H), 3.64 (s, 3H).

EXAMPLE 12 methyl 4'-(aminomethyl)biphenyl-2-carboxylate hydrochloride

10% palladium-carbon (180 mg) was added to the compound (370 mg) prepared in Example 11 in methanol (6 mL) solution and stirred overnight under hydrogen atmosphere at room temperature. The reaction mixture was substituted with argon gas and filtered with celite (trade name), and then concentrated. 4 mol/L hydrochloric acid in ethyl acetate solution (1 mL) was added to the obtained residue that was dissolved to ethyl acetate (10 mL) and stirred, and then concentrated to obtain the tided compound (380 mg) having the following physical data by washing the obtained residue with ethyl acetate and hexane.

NMR (CDCl3): δ 8.40-8.10 (brs, 3H), 7.76 (dd, J=7.6, 1.4 Hz, 1H), 7.68-7.59 (m, 1H), 7.55-7.31 (m, 6H), 4.14-4.02 (m, 2H), 3.61 (s, 3H).

EXAMPLE 13

4'-{[(phenylacetyl)amino]methyl}-1,1'-biphenyl-2-carboxylic acid

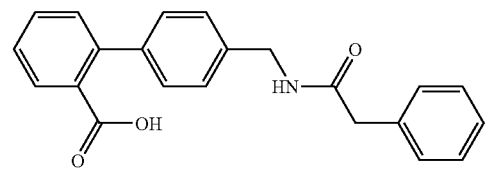 [SMILES: O=C(Cc1ccccc1)NCc1ccc(-c2ccccc2C(=O)O)cc1]

The titled compound having the following physical data was obtained by the same procedures as a series of Example 6 and Example 7 using the compound prepared by Example 12 instead of the compound prepared by Example 5 and using phenylacetyl chloride instead of pentanoyl chloride.

TLC: Rf 0.67 (chloroform:methanol=8:2);

NMR (CDCl3): δ 7.94 (dd, J=1.2, 7.6 Hz, 1H), 7.60-7.14 (m, 12H), 5.91-5.80 (br, 1H), 4.43 (d, J=6.0 Hz, 2H), 3.63 (s, 2H).

BIOLOGICAL EXAMPLE

The following experiments proved that the compound of the present invention has BLT2 binding activity and that BLT2 expresses in keratinocytes, and the function.

All processes are based on basic and genetic engineering techniques, e.g., the preparation of gene high-expressing cells and routine procedures. Further, the measurement accuracy and/or snesitometry of the measuring method of the present invention were improved to evaluate the compound of the present invention as follows. The detailed experimental methods were shown as follows.

Biological Example 1

Evaluation of BLT2 Antagonistic Activity by Monitoring the Variation of Intracellular $Ca^{2+}$ Concentration The receptor antagonist activity was evaluated by using human BLT2 gene-overexpressing Chinese Hamster Ovar (CHO) cells (see J. Exp. Med. Volume 192, Number 3 2000, and 421-.). BLT2-expressing cells were cultured in Ham's F1 medium (GIBCO BRL and No. 11765-047) containing 10% FBS (fetal bovine serum), penicillin/streptomycin and blasticidin (5 μg/ml). First, to make the cells to take Fura2-AM (Dojindo and No. 348-05831), the cells were incubated in 5 μM Fura2-AM solution (Ham's F1 medium containing 10% FBS, 20 mM HEPES buffer (pH7.4) and 2.5 mM probenecid (Sigma and No. P-8761)) at 37° C. for 60 minutes. Then, the cells were washed once with Hanks solution containing 20 mM HEPES buffer (pH7.4) and 2.5 mM probenecid, and soaked in Hanks solution until assay. The plate was sat up on fluorescent drug screening system (Hamamatsu Photonics FDSS-2000) and measured without any stimulation for 30 seconds, to which the compound solution of the present invention was added. LTB4 (final concentration: 3 μM) was added to the plates 3 minutes later, of which the intracellular calcium ion concentration around the addition were measured at 3 seconds intervals (excitation wavelength 340 nm, 380 nm and fluorescent wave-length 500 nm). The compound of the present invention was dissolved to dimethylsulfoxide (DMSO) and added in order that the final concentration is nM-10 μM. BLT2 antagonistic activity was calculated by being compared the difference a value before addition of LTB4 and a value after the addition in cells processed with the compound with a peak value of LTB4 in a well containing DMSO as control value (A) (Inhibition ratio (%)={(A−B)/A}×100). $IC_{50}$ value is a concentration of the compound of the present invention in which the inhibition ratio is 50%. Also, BLT1 antagonistic activity was measured by the same way. For example, $IC_{50}$ value for BLT2 of the compound prepared in Example 1(32) is 1.8 μM and the compound did not have BLT1 antagonistic activity.

Biological Example 2

Evaluation of BLT2 Agonistic Activity by Monitoring the Variation of Intracellular $Ca^{2+}$ Concentration The compound of the present invention (final concentration: 1-10 μM, dimethylsulfoxide (DMSO)) was added 3 minutes later, and the intracellular calcium ion concentrations around addition of LTB4 were measured at 3 seconds intervals (excitation wavelength 340 nm, 380 nm and fluorescent wave-length 500 nm). BLT2 agonistic activity was calculated by being compared a rising value (D) of fluorescent ratio after addition of a subject compound from a value before addition with a peak value of LTB4 stimulation in a well containing DMSO instead of a subject compound as control value (C) (a rate of increase of intracellular $Ca^{2+}$ concentration (%)=(D/C)×100). The $EC_{50}$ value was calculated by calculating the rate of increase in each concentration of the compound. Also, BLT1 antagonistic activity was measured by the same way.

For example, $IC_{50}$ value for BLT2 of the compound prepared in Example 13 is 0.045 μM and the compound did not have BLT1 agonistic activity.

Biological Example 3

Mouse BLT2 Expression in CHO Cells mBLT2 ORF was amplified by PCR using a sense primer having BamHI restriction enzyme site (sense primer; 5'-CGGGATCCCGCATGTCTGTCTGCTACCGTC-3' (SEQ ID NO.1)) and an antisense primer having EcoRI restriction enzyme site (antisense primer; 5'-CGGAATTC-TACCATFCTTGACTGTCTT-3' (SEQ ID NO.2)). The PCR product was digested with BamHI and EcoRI and inserted in expression plasmid (pcDNA3 Invitrogen). The inserted sequence was confirmed by the DNA sequence. Plasmid DNA (31 g) was transfected into CHO cells cultured in Ham's F-12 medium containing 10% fetal bovine serum and antibiotic (streptomycin (100 μg/mL) and penicillin (100 μg/L)) in cell culture plates (6 cm). The resistant strains were obtained by culturing for 2 weeks in the existence of antibiotic (G418 [Wako], 1 mg/mL). The stable expressing strains were obtained by culturing 19 obtained resistant strains with limiting dilution method.

Biological Example 4

Northern Blotting

Each mouse tissue BLT2 mRNA was northern-blotted to explore the expression pattern. First, total RNA of mouse tissue (C57B1/6J Jc1 [Japan clea]) was extracted using RNA extraction reagent (Isogen [Wako]). Also, mouse peritoneal macrophages were collected 4 days later by injecting thioglycolate (4.05 w/v %, 2 mL) into mouse peritoneal cavity. Mouse neutrophils were collected 7 hours later by injecting casein (2.0 w/v %, 2 mL) into mouse peritoneal cavity. Poly $(A)^+$ RNA was separated from total RNA (200 μg) with mRNA extraction kit (μMACS mRNA isolation kit [Miltenyi Biotec]). Mouse tissue mRNA (5 μg), total RNA (10 μg) of macrophages and neutrophils was degenerated and transfered nylon membrane filter (Hybond N+[Amersham Biosciences]) after 0.7% formaldehyde agarose gel electrophoresis. $^{32}$P-dCTP-labeled mBLT2 or glyceraldehydes-3-phosphate dehydrogenase (g.3PDH) ORF was hybridized for 2 hours at 65° C. and washed with 2×SSC and 0.1% SDS. Then, it was washed for 20 minutes (at 65° C.) with 0.2×SSC, 0.1% SDS and 1 hour (at 68° C.) with 0.1×SSC, 0.1% SDS. Then, it was washed for 20 minutes (at 65° C.) with 0.2×SSC and 0.1% SDS, and 1 hour (at 68° C.) with 0.1×SSC and 0.1% SDS. It was autoradiographied for 7 days.
<Result>
The result of northern analysis revealed that mBLT2 mRNA was expressed in small intestine and skin. The main transcript was 1.5 kb and 6.7 kb. FIG. 1 shows the result.

Biological Example 5

Quantitative Real-Time RT-PCR

Figure 2:
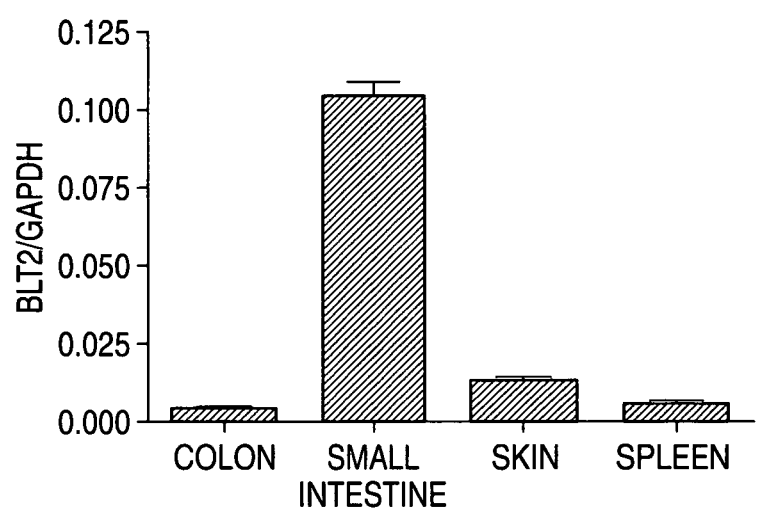
FIG. 2 shows the amount of BLT2 mRNA expression in each mouse tissue (quantitative real time RT-PCR).

Quantitative real-time RT-PCR was carried out to measure the expression of BLT2 mRNA in each mouse tissue. First, cDNA was synthesized (Superscript II [Invitrogen]) from mouse tissue mRNA (50 ng), total RNA (50 ng) of macrophages and neutrophils, and diluted 100 times with distilled water. Then, the cDNA was amplified in 20 μL microcapillary as PCR solution containing diluted cDNA (5 L), 1xFastStart DNA Master SYBR Green I (Roche; Molecular Biochemicals), MgCl$_2$(final concentration 4 mM) and primers (0.5 µM) by PCR (LightCyclerSystem[Roche Molecular Biochemicals]). Also, pCXN2-mBLT2 and pcDNA3.1 (containing mG3PDH cDNA) were used as controls and the following were used as a primer; mBLT2 820+, 5'-ACAGCCTFGGCT-TCTTCAG-3' (SEQ ID NO.3); mBLT2 1013-, 5'-TGC-CCCATTACTTTCAGCIT-3' (SEQ ID NO.4); GAPDH-1013+, GTGGACCTCATGGCCTACAT-5'(SEQ ID NO.5); GAPDH-1226-, 5'-GGGTGCAGCGAACTTTATTG-3' (SEQ ID NO.6). Using the attached analytical software for LightCycler after PCR, each mRNA amount of BLT2 and G3PDH was calculated based on the signal and frequency of SYBR Green I as indicators.
<Result>
As the result of correcting the mRNA amount of BLT2 with the mRNA amount of G3PDH, it was revealed that BLT2 mRNA was extremely high-expressed in small intestine and secondary-expressed in skin, and low-expressed in large intestine and spleen. FIG. 2 shows the result.

Biological Example 6

In Situ Hybridization

Paraffin sections of mouse (C57B1/6J Jc1 [Japan clea]) skin sample were fixed by 10% formalin containing PBS, of which BLT2 mRNA expressions were observed by non-radioactive in situ hybridization. First, the paraffin-embedded mouse tissues were cut into 4 µm thickness and mounted on silane coated glass, and deparaffinized. Afterwards, the samples were prepared by being processed by proteinase K (5 µg/L in PBS) (for 10 minutes at room temperature) and being processed by glycine (2 mg/mL in PBS) (for 15 minutes at room temperature.). The samples were acetylated in acetic anhydride (1 mL in 400 mL of 0.1M triethanolamine, pH8.0) for 15 minutes at room temperature and washed with PBS and soaked in 50% formamide containing 2×SSC, and then hybridized. mBLT2 ORF fragment (741-941) was amplified by PCR using a downstream primer containing HindIII restriction enzyme site and an upstream primer containing EcoRI restriction enzyme site and inserted into vector (pSPT18) by directional cloning system. An antisense probe was prepared by digesting them with HindIII and a sense probe was prepared by digesting them with EcoRI. These probes were digoxigenin-11-UTP-labeled with DIG RNA labeling kit (Roche Molecular Biochemicals). They were hybridized under humidification for 16 hours at 42° C. The samples were washed 3 times using 50% formamide containing 2×SSC for 20 minutes at 42° C. Non-hybridized probes were digested by enzyme (RNaseA (20p g/mL) in NaCl (500 mM), EDTA (1 mM) and Tris-HCl (10 mM, pH8.0)) for 30 minutes at 37° C.
Further, the samples were visualized by digoxigenin-labeled probes prepared according to the attached manual using DIG nucleic acid detection kit (Roche Mollecular Biochemical). And, they were counterstained by methyl green.
<Result>
FIG. 3 shows the result of 1n Situ hybridization. A, C and E show the result of hybridization with mBLT2 antisense probes and B, D and F show the result of hybridization with sense control probes (Magnification: A, B=140 times; C, D=240 times; E, F=430 times). These results revealed that mBLT2 is expressed in hair epidermal hair follicle keratinocytes and folicle keratinocyte.

Biological Example 7

Figure 4:
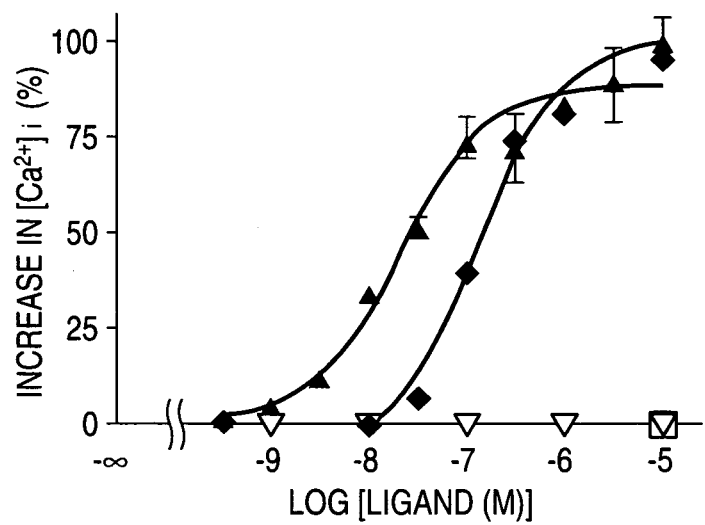
FIG. 4 shows the rise of intracellular calcium concentration when BLT2-expressing cells are processed by BLT2 agonist.

Measurement of Intracellular Ca$^{2+}$ Concentration mBLT2-expressing CHO cells prepared by Biological Example 3 were cultured in modified Hepes-Tyrode's BSA buffer (Hepes-NaOH (25 mM, pH7.4), NaCl (140 mM), KCl (2.7 mM), CaCl$_2$(10 nM), NaHCO$_3$(12 mM), D-Glucose (5.6 mM), NaH$_2$PO$_4$(0.37 mM), MgCl$_2$(0.49 mM), cremophour (0.01%), fatty acid-free BSA (fraction V, 0.1w/v %)) containing fluorochrome (Fura-2 AM [Dojin], 3 µm) at 37° C. for 2 hours to make to take fluorochrome. These cells were washed 2 times and resuspended (106 cells/mL) in Hepes-Tyrode's BSA buffer. The cell suspension (0.5 mL) was applied to fluorescent intensity meter (CAF-100 system [Jasco]). Dimethylsulfoxide (DMSO) solution (5 µL) containing ligand was added to the cell suspension, of which the intracellular calcium concentration was monitored (excitation wavelength 340 nm and 380 nm and fluorescent wave-length 510 nm).
<Result>
FIG. 4 shows a graph of the rise of the intracellular calcium concentration using the compound prepared in Example 9 as a ligand (hereafter, it is abbreviated to compound A). Compound A (filed triangle) indicated EC$_{50}$ value (compound A: 21 nM; LTB4: 121 nM) lower than that of LTB4(filed Diamond). The intracellular calcium concentration was not rised though compound A was added to mBLT1-expressing CHO cells (opened triangle) and mock (opened square).

Biological Example 8

Isolation and Culture of Mouse Keratinocytes 4 weeks mouse (C57B1/6J Jc1 [Japan clea]) skin sections were soaked at 4° C. overnight in dispase solution (250 PU/mL dispase in PBS). The epidermals were flaked off from the dermis and separated for 5 minutes using 0.05% trypsin-EDTA. Trypsin was inerted in 10% MEM medium (Sigma). After centrifugal separation, the cells were suspended to Defined keratinocyte-SFM medium containing E.G.F (10 ng/mL) and cholera toxin (10 pM).

Biological Example 9

Figure 5:
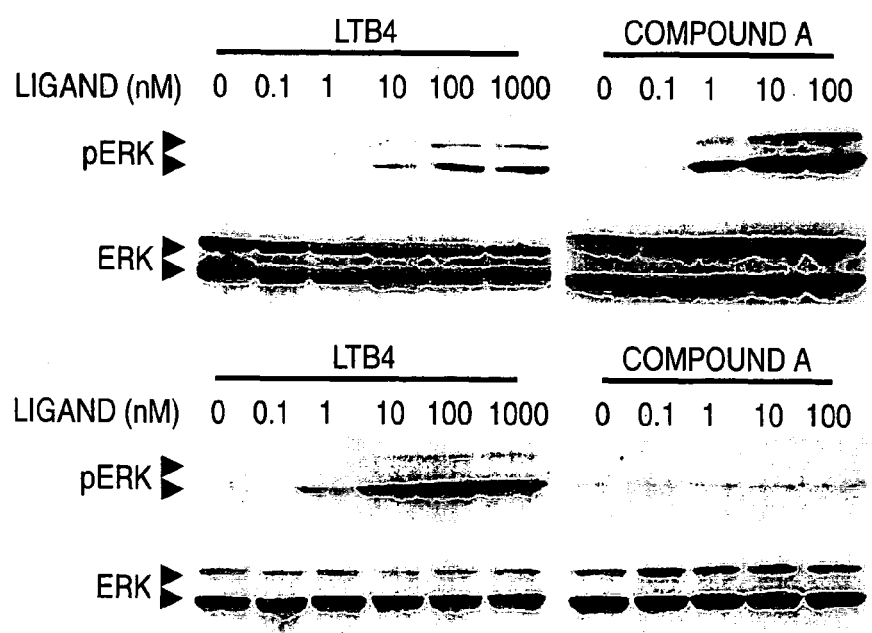
FIG. 5 shows ERK phosphorylation activity when BLT1 or BLT2-expressing cells are processed by BLT2 agonist.

ERK phosphorylation (1)

mBLT2-expressing CHO cells prepared in Biological Example 3 were cultured in 12 well-culture plate at cell density of 2.0×10$^5$ cell/well. The cells were transfered to F-12 medium containing 0.1% BSA 2 days later and cultured without serum for 12 hours. The cells were preincubated in F-12 medium containing 0.1% BSA for 10 minutes and exposed to various concentrations of ligand for 5 minutes. After removing the medium, the cells were digested by lysis buffer (Tris-HCl (20 mM), β-glycerophosphate (50 mM), EGTA (5 mM), Na$_3$VO$_3$(1 mM), DTT (2 mM), PMSF (1 µM), NP-40(1%), 250 µL) and frozen at −80° C. After melting, they were dissolved by passing through 27 gauge needle 10 times. The cell lysate was heat-denatured for 10 minutes at 100° C. and transfered to nitrocellulose membrane (Hybond ECL) using semi-dry transfer cell (SEMI-DRY TRANSFER CELL [Bio-Rad]) after 12% acrylamide SDS-PAGE. The membrane was blocked at 4° C. overnight using blocking liquid (Tween 20(0.1 v/v %), tris-buffered saline containing skim milk (0.1 w/v % for ERK; 5 w/v % for phospho-ERK)). Then, the membrane was incubated in blocking buffer containing 1000 times diluted primary antibody (anti-phospho-ERK antidbody (phospho-p44/p42 MAPK (Thr202/tyr204) antibody [Cell Signaling TECHNOLOGY]) and anti-ERK antibody (p44/p42 MAP Kinase Antibody[Cell Signaling TECHNOLOGY])) for 2 hours and reacted with 2000 times diluted second HRP-labeled antibody and then detected using ECL system (Amersham).
<Result>
FIG. 5 shows ERK phosphorylation when mBLT2-expressing CHO cells and mBLT1-expressing CHO cells were stimulated with LTB4 or compound A (upper row: mBLT2-expressing CHO cells; lower row: mBLT1-expressing CHO cells). ERK phosphorylations in mBLT2-expressing CHO cells and mBLT1-expressing CHO cells were induced by LTB4 and compound A. ERK phosphorylation in BLT1-expressing CHO cells was induced by compound A.

Biological Example 10

Immunocytochemical Stain

Figure 6:
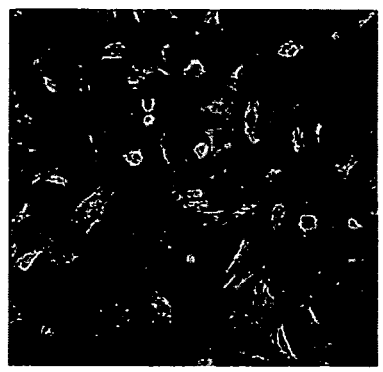
FIG. 6 shows that alpha-keratin 5 expresses in primary culture keratinocytes prepared from mouse skin.
Figure 6:
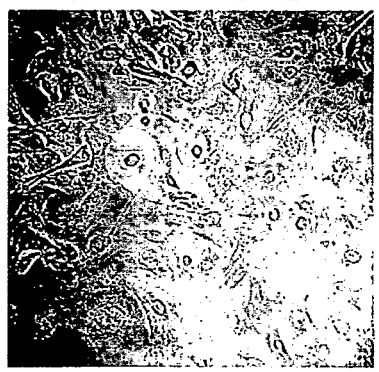
Figure 6:
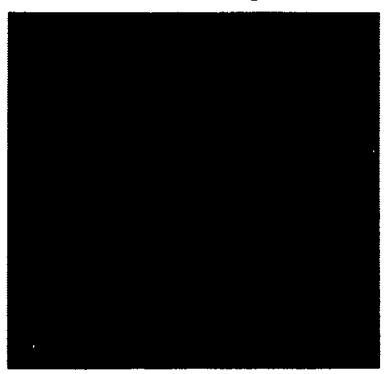
Figure 6:

The cells prepared in Biological Example 8 were cultured in chamber slide and fixed by fixative (methanol:acetone=1: 1). They were washed with PBS and blocked in PBS containing 10% goat serum and 3% BSA. Then, the specimens were dyed using antibody to mouse keratin 5(mouse keratin 5 [Covance Research Products]) (1 μg/ml) and second fluorescent-labeled antibody (Alexa Fluor R546 anti-rabbit IgG [Molecular probes], 10 μg/mL) and observed with fluorescence microscope.
<Result>
Most cells prepared from mouse was mouse keratin 5-positive. Therefore, the result revealed that these cells are keratinocytes. FIG. 6 shows the result.

Biological Example 11

ERK Phosphorylation (2)

Figure 7:
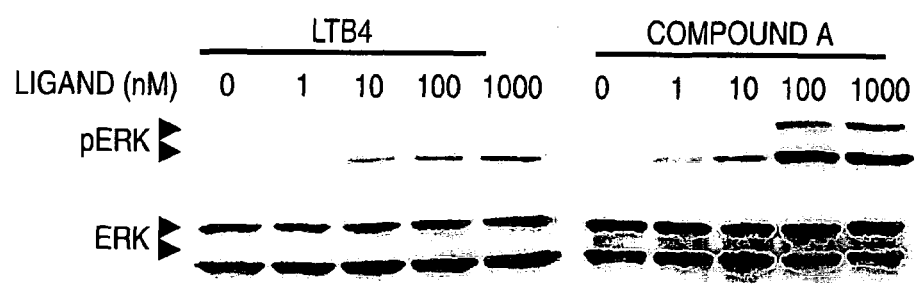
FIG. 7 shows ERK phosphorylation activity when primary culture keratinocytes prepared from mouse skin are processed by BLT2 agonist.

The primary culture keratinocytes prepared in Biological Example 8 were cultured in 12-well culture plate at cell density of 4.0×1 cell/well. They were transfered to Defined keratinocyte SFM medium (GibcoBRL) 1 day later from culture and cultured without serum for 12 hours. The cells were preincubated for 10 minutes in Defined keratinocyte SFM medium containing 0.1% BSA and stimulated as well as Biological Example 9, of which ERK phosphorylation was observed.
<Result>
FIG. 7 shows ERK phosphorylation when mouse primary culture keratinocytes were stimulated with LTB4 or compound A. LTB4 and compound A induced ERK phosphorylation of mouse primary culture keratinocytes.

FORMULATION EXAMPLE

Typical formulation examples used in the present invention are shown as follows.

Formulation Example 1

4'-{[pentanoyl(phenyl)amino]methyl}-1,1'-biphenyl-2-carboxylic acid (100 g), carboxymethylcellulose calcium, magnesium stearate and microcrystalline cellulose were admixed in conventional method and punched out to obtain 10,000 tablets each containing 10 mg of the active ingredient.

Formulation Example 2

4'-{[pentanoyl(phenyl)amino]methyl}-1,1'-biphenyl-2-carboxylic acid, mannitol (2 kg) and distilled water (50 L) were admixed in a conventional method and filtered with dust removal filter and placed at 5 mL into ampoules. The ampoules were heat-sterilized by autoclave to thereby obtain 10,000 ampoules each containing 20 mg of the active ingredient.
Industrial Applicability
Since BLT2 is highly expressed in keratinocyte, a compound with BLT2 binding activity, salt thereof, solvate thereof or prodrug thereof is useful for prevention and/or therapy for skin disease. The compound represented in formula (I), salt thereof, solvate thereof or prodrug thereof is useful for prevention and/or therapy of BLT2 mediated diseases, e.g., dermatosis, intestinal disease, HIV infection, acquired immunodeficiency syndrome, rejection to transplant, transplant rejection, graft-versus-host disease, autoimmune disease, allergic disease, inflammation, infection, ulcers, lymphoma, malignant tumor, leucaemia, arterial sclerosis, hepatitis, hepatic cirrhosis or cancer, etc.

The invention claimed is:

1. A compound of 4'-{[pentanoyl(phenyl)amino]methyl}-1,1'-biphenyl-2-carboxylic acid or a salt thereof or an ester thereof.

2. A pharmaceutical composition comprising the compound according to claim 1, a salt thereof, or an ester thereof, as an active ingredient together with an inert diluent.

* * * * *

SEQUENCE LISTING

<160> NUMBER OF SEQ ID NOS: 6

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1
cgggarcccg catgtctgtc tgctaccgtc        30

<210> SEQ ID NO 2
<211> LENGTH: 27
<212> TYPE: DNA
<213> ORGANISM: Artificial
<220> FEATURE:

```
<223> OTHER INFORMATION: primer

<400> SEQUENCE: 2
cggaattcta ccattcttga ctgtctt                                              27

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
acagccttgg ctttcttcag                                                      20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
tgccccatta ctttcagctt                                                      20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
gtggacctca tggcctacat                                                      20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gggtgcagcg aactttattg                                                      20
```